US005707607A

United States Patent [19]
Quay

[11] Patent Number: 5,707,607
[45] Date of Patent: Jan. 13, 1998

[54] PHASE SHIFT COLLOIDS AS ULTRASOUND CONTRAST AGENTS

[75] Inventor: Steven C. Quay, Pacific Palisades, Calif.

[73] Assignee: Sonus Pharmaceuticals, Inc., Bothell, Wash.

[21] Appl. No.: 469,472

[22] Filed: Jun. 6, 1995

Related U.S. Application Data

[60] Division of Ser. No. 148,284, Nov. 8, 1993, Pat. No. 5,595,723, which is a continuation-in-part of Ser. No. 008,172, Jan. 25, 1993, Pat. No. 5,558,855.

[51] Int. Cl.$^6$ .................................................. A61B 8/13
[52] U.S. Cl. ..................................... 424/9.52; 128/662.02
[58] Field of Search ............................ 424/9.5, 9.51, 424/9.52; 128/662.02

[56] References Cited

U.S. PATENT DOCUMENTS

| | | |
|---|---|---|
| 3,898,843 | 8/1975 | Chabert et al. . |
| 4,265,251 | 5/1981 | Tickner et al. . |
| 4,276,885 | 7/1981 | Tickner et al. . |
| 4,442,843 | 4/1984 | Rasor et al. . |
| 4,466,442 | 8/1984 | Hilmann et al. . |
| 4,533,254 | 8/1985 | Cooke et al. . |
| 4,544,545 | 10/1985 | Ryan et al. . |
| 4,572,203 | 2/1986 | Feinstein . |
| 4,657,756 | 4/1987 | Rasor et al. . |
| 4,681,119 | 7/1987 | Rasor et al. . |
| 4,684,479 | 8/1987 | D'Arrigo . |
| 4,718,433 | 1/1988 | Feinstein . |
| 4,767,610 | 8/1988 | Long . |
| 4,774,958 | 10/1988 | Feinstein . |
| 4,832,941 | 5/1989 | Berwing et al. . |
| 4,844,882 | 7/1989 | Widder et al. . |
| 4,859,363 | 8/1989 | Davis et al. . |

(List continued on next page.)

FOREIGN PATENT DOCUMENTS

| | | | |
|---|---|---|---|
| 8930351 | 8/1989 | Australia . | |
| 9170982 | 10/1991 | Australia | A61B 008/00 |
| 87105799 | 4/1988 | China | A61K 049/02 |
| 0077752 | 4/1983 | European Pat. Off. | A61K 49/00 |
| 0231091 | 8/1987 | European Pat. Off. | A61K 9/10 |
| 0245019 | 11/1987 | European Pat. Off. | A61K 49/00 |
| 0307087 | 3/1989 | European Pat. Off. | A61K 31/02 |
| 0324938 | 7/1989 | European Pat. Off. | A61K 49/00 |
| 0327490 | 8/1989 | European Pat. Off. | A61K 49/00 |
| 0357163 | 3/1990 | European Pat. Off. | A61K 49/00 |
| 0359246 | 3/1990 | European Pat. Off. | A61K 49/00 |
| 0454044 | 10/1991 | European Pat. Off. | A61K 9/14 |
| 0458745 | 11/1991 | European Pat. Off. | A61K 49/00 |
| 0494615 | 7/1992 | European Pat. Off. | A61K 49/00 |
| 0502814 | 9/1992 | European Pat. Off. | G01R 33/28 |
| 0467031 | 10/1992 | European Pat. Off. | A61K 49/00 |
| 0554213 | 8/1993 | European Pat. Off. | A61K 49/00 |
| 4100470 | 3/1925 | Germany | 120/5 |
| 3834705 | 4/1990 | Germany | A61K 49/00 |
| 4127442 | 2/1993 | Germany | A61K 9/127 |

(List continued on next page.)

OTHER PUBLICATIONS

American Heart Association, Abstracts of the 58th Scientific Sessions, Circulation 72:Oct. 1985 III–427.

Association of University Radiologists, Proceedings of the Association of University Radiologists Annual Meeting 1982, Journal of Clinical and Laboratory Research Investigative Radiology 17:4, PS28, Abstract 110 (Jul.–Aug. 1982).

Bleeker, et al., On the Application of Ultrasonic Contrast Agents for Blood Flowmetry and Assessment of Cardiac Perfusion, Journal of Ultrasound in Medicine 9:461–471, 1990.

Bleeker, et al., Ultrasonic Characterization of Albunex, A New Contrast Agent, Journal Acoustical Society of America 87:1792–1797 (1990).

Davis, et al., Echogenicity Cause By Stable Microbubbles in a Protein–Lipid Emulsion, The Journal of Clinical Ultrasound 9:249–252, Jun., 1981.

De Jong, et al., Absorption and Scatter of Encapsulated Gas Filled Microspheres: Theoretical Consideration and Some Measurements, Ultrasonics 30:95–103 (1992).

De Jong, et al., Principles and Recent Developments in Ultrasound Contrast Agents, Ultrasonics 29:324–330 (Jul., 1991).

Epstein, et al., On the Stability of Gas Bubbles in Liquid–Gas Solutions, Journal of Chemical Physics 18:1505–1509 (Nov., 1950).

Feinstein, et al., Safety and Efficacy of a New Transpulmonary Ultrasound Contrast Agent: Initial Multicenter Clinical Results, Journal of American College of Cardiology 16:316–24 (Aug., 1990).

Feinstein, et al., Microcardial Contrast Echocardiography: Examination of Infracoronary Injections. Microbubble Diameters and Video Intensity Decay, American Journal of Physiologic Imaging 1:12–18 (1986).

Fobbe, et al., Farbkodierte Duplexsonographie Und Ultraschallkontrastimittel–Nachweis Von Renalen Perfusionsdefekten Im Tierexperiment, Fortschr. Röntgenstr. 154:242–245 (1991).

(List continued on next page.)

*Primary Examiner*—Gary E. Hollinden
*Attorney, Agent, or Firm*—Limbach & Limbach L.L.P.

[57] ABSTRACT

Agents for enhancing the contrast in a diagnostic ultrasound procedure comprise colloidal dispersions of the liquid-in-liquid type, i.e., emulsions or microemulsions, in which the dispersed liquid phase is a high vapor pressure chemical which undergoes a phase change from a dispersed liquid to a highly echogenic dispersed gaseous foam or kugelschaum following administration to an organism. The liquid state of the dispersed phase allows one to manufacture extremely stable, pharmaceutically acceptable emulsions with particle sizes typically below 1000 nm. The gaseous state at body temperature yields highly echogenic microbubbles, typically below 10,000 nm in diameter, which are effective as ultrasound contrast agents. Intravenous, intraarterial, oral, intraperitoneal, and intrauterine dosage forms, methods of administration, and imaging techniques are described.

6 Claims, No Drawings

U.S. PATENT DOCUMENTS

| | | |
|---|---|---|
| 4,865,836 | 9/1989 | Long. |
| 4,895,876 | 1/1990 | Schweighardt et al.. |
| 4,900,540 | 2/1990 | Ryan et al.. |
| 4,927,623 | 5/1990 | Long. |
| 4,957,656 | 9/1990 | Cerny et al.. |
| 4,987,154 | 1/1991 | Long. |
| 4,993,415 | 2/1991 | Long. |
| 5,078,146 | 1/1992 | Sato. |
| 5,080,885 | 1/1992 | Long. |
| 5,088,499 | 2/1992 | Unger. |
| 5,107,842 | 4/1992 | Levine et al.. |
| 5,114,703 | 5/1992 | Wolf et al.. |
| 5,123,414 | 6/1992 | Unger. |
| 5,137,928 | 8/1992 | Erbel et al.. |
| 5,141,738 | 8/1992 | Rasor et al.. |
| 5,147,631 | 9/1992 | Glagch et al.. |
| 5,155,215 | 10/1992 | Ranney. |
| 5,171,755 | 12/1992 | Kaufman. |
| 5,205,290 | 4/1993 | Unger. |
| 5,260,496 | 11/1993 | Meinert et al.. |
| 5,271,928 | 12/1993 | Schneider et al.. |
| 5,281,408 | 1/1994 | Unger. |
| 5,284,645 | 2/1994 | Long. |
| 5,344,930 | 9/1994 | Riess et al.. |
| 5,354,549 | 10/1994 | Klaveness et al.. |
| 5,385,147 | 1/1995 | Anderson et al.. |
| 5,393,513 | 2/1995 | Long, Jr.. |
| 5,401,493 | 3/1995 | Lohrmann et al.. |
| 5,403,575 | 4/1995 | Kaufman et al. ........... 424/1.89 |
| 5,406,950 | 4/1995 | Brandenburger et al.. |
| 5,409,688 | 4/1995 | Quay ............................. 424/9.52 |
| 5,413,774 | 5/1995 | Schneider et al. ........... 424/9.51 |
| 5,505,932 | 4/1996 | Grinstaff et al. ............. 424/9.3 |
| 5,536,489 | 7/1996 | Lohrmann et al. ........... 424/9.52 |
| 5,536,490 | 7/1996 | Klaveness et al. ........... 424/9.52 |
| 5,540,909 | 7/1996 | Schutt .......................... 424/9.52 |

FOREIGN PATENT DOCUMENTS

| | | | |
|---|---|---|---|
| 64-325 474 | of 0000 | Japan | A61K 49/00 |
| 2196730 | 10/1982 | Japan | A61K 49/00 |
| 59067229 | 4/1984 | Japan | A61K 049/04 |
| 63-60943 | 3/1988 | Japan | A61K 49/00 |
| 57-177790 | 8/1990 | Japan | A61K 49/00 |
| 1641280 | 4/1991 | U.S.S.R. | A61B 8/00 |
| 1718798 | 3/1992 | U.S.S.R. | A61B 005/00 |
| WO 80/02365 | 11/1980 | WIPO | A61B 10/00 |
| WO 89/06978 | 8/1989 | WIPO | A61K 49/00 |
| WO 89/10118 | 11/1989 | WIPO | A61K 31/02 |
| WO 90/07491 | 7/1990 | WIPO | C07C 233/88 |
| WO 91/09629 | 7/1991 | WIPO | A61K 49/00 |
| WO 91/12823 | 9/1991 | WIPO | A61K 49/00 |
| WO 91/15244 | 10/1991 | WIPO | A61K 49/00 |
| WO 91/18612 | 12/1991 | WIPO | A61K 31/70 |
| WO 92/02560 | 2/1992 | WIPO | C08F 2/38 |
| WO 92/05806 | 4/1992 | WIPO | A61K 49/00 |
| WO 92/08496 | 5/1992 | WIPO | A61K 49/00 |
| WO 92/11873 | 7/1992 | WIPO | A61K 49/00 |
| WO 92/15284 | 9/1992 | WIPO | A61K 9/127 |
| WO 92/17212 | 10/1992 | WIPO | A61K 49/00 |
| WO 92/17213 | 10/1992 | WIPO | A61K 49/00 |
| WO 92/18165 | 10/1992 | WIPO | A61K 49/00 |
| WO 92/18169 | 10/1992 | WIPO | A61K 49/04 |
| WO 92/21382 | 12/1992 | WIPO | A61K 49/00 |
| WO 92/22247 | 12/1992 | WIPO | A61B 8/00 |
| WO 93/00930 | 1/1993 | WIPO | A61K 49/00 |
| WO 93/00933 | 1/1993 | WIPO | A61K 49/00 |
| WO 93/01798 | 2/1993 | WIPO | A61K 9/00 |
| WO 93/05819 | 4/1993 | WIPO | A61K 49/00 |
| WO 93/06869 | 4/1993 | WIPO | A61K 31/715 |
| WO 93/07905 | 4/1993 | WIPO | A61K 47/48 |
| WO 93/17718 | 9/1993 | WIPO | A61K 49/00 |
| WO 94/06477 | 3/1994 | WIPO | A61K 49/00 |
| WO 94/09625 | 5/1994 | WIPO | |
| WO 94/09829 | 5/1994 | WIPO | A61K 49/00 |
| WO 94/16742 | 8/1994 | WIPO | A61K 49/04 |
| WO 94/19101 | 9/1994 | WIPO | B01J 13/00 |
| WO 94/21301 | 9/1994 | WIPO | A61K 49/00 |
| WO 94/21302 | 9/1994 | WIPO | A61K 49/00 |
| WO 94/21303 | 9/1994 | WIPO | A61K 49/00 |
| WO 94/22368 | 10/1994 | WIPO | A61K 5/055 |
| WO 94/28780 | 12/1994 | WIPO | |
| WO 94/28797 | 12/1994 | WIPO | A61B 8/00 |
| WO 94/28873 | 12/1994 | WIPO | A61K 9/127 |
| WO 94/28874 | 12/1994 | WIPO | A61K 9/127 |
| WO 94/28939 | 12/1994 | WIPO | A61K 49/00 |
| WO 95/01187 | 1/1995 | WIPO | A61K 49/00 |
| WO 95/03835 | 2/1995 | WIPO | A61K 49/00 |

OTHER PUBLICATIONS

Handa, et al., Phospholipid Monolayers at the Triolein–Saline Interface: Production of Microemulsion Particles and Conversion of Monolayers to Bilayers, Biochemistry 29: 2884–2890 (1990).

Kabalnov, et al., Safety and Efficacy of a New Transpulmonary Ultrasound Contrast Agent: Initial Multicenter Clinical Results, Journal of Fluorine Chemistry 50: 271–284 (1990), Keller, et al., Successful Left Ventricular Opacification Following Peripheral Venou Injection of Sonicated Contrast Agent: An Experimental Evaluation, American Heart Journal, 115: 4: 570–575 (Sep. 1987).

Long, et al., Experiments With Radiopaque Perfluorocarbon Emulsions For Selective Opacification of Organs and Total Body Angiography, Investigative Radiology 15:242–247 (1980).

Marshall, Encyclopedie Des Gaz. Encyclopedia of Gas, 1976.

Mattrey, et al., Gas Emulsions as Ultrasound Contrast Agents Preliminary Results in Rabbits and Dogs, Investigative Radiology, 29: S139–S141 (Jun. Supplement 1994).

Meltzer, et al., Transmission of Ultrasonic Contrast Through the Lungs, Ultrasound in Med. & Biol., vol. 7, No. 4, pp. 377–384 (1981).

Meltzer, et al., Why Do The Lungs Clear Ultrasonic Contrast? Ultrasound in Medicine and Biology 6:263–269 (1980).

Ohta, et al., Effect of the Contrast Agent and the Agitation Method on the Size, Number and Stability of Microbubbles: A Basic Experiment for the myocardial Contrast Study, Japanese Journal of Medical Ultrasonics 18:318–325 (1991).

Ophir, et al., Contrast Agents in Diagnostic Ultrasound, Ultrasound in Medicine and Biology, 15:319–333 (1989).

Schubert, et al., Microemulsifying Fluorinated Oils With Mixtures of Fluorinated and Hydrogenated Surfactants, Colloids and Surgaces: Physicochemical and Engineering Aspects 84:97–106 (1994) (submitted as a communication).

Schlief, Ultrasound Contrast Agents, Current Opinion in Radiology 3:198–207 (1991).

Serratrice, et al., Co–Solubilisation De Fluorocarures Et D'Eau En Présence De Nouveaux Tensioactifs Non Ionioues Fluores, Journal Chim. Phys. 87:1969–1980 (1990).

Swanson, et al., Pharmaceuticals in Medical Imaging; Radiopaque Contrast Media Radiopharmaceuticals Enhancement Agents for Magnetic Resonance Imaging and Ultrasound, Macmillian Publishing Co., Inc., pp.682–685 (1990).

Szönyi, et al., Syntheses De Tensioactifs F–Alkyles Non Ioniques Monodisperses, Journal of Fluorine Chemistry 36:195–209 (1987).

Verescon, et al., An Easy, Convenient Way of Describing the Stability of Fluorocarbon Emulsions, Journal of de Chimie Physique 86:2111–2116 (1989).

Violante, et al., Particle Stabilized Bubbles for Enhanced Organ Ultrasound Imaging, Investigative Radiology 26:194–200 (Nov. 1991).

Widder, et al., Microbubbles as a Contrast Agent for Neurosonography and Ultrasound–Guided Catheter Manipulation: In Vitro Studies, AJR 147:347–352 (Aug. 1986).

Zarif, et al., Synergistic Stabilization of Perfluorocarbon–Pluronic F–68 Emulsion By Perfluoroalkylated Polyhydroxylated Surfactants, JAOCKS 66:10 (Oct. 1989).

Ziskin, et al., Contrast Agents for Diagnostic Ultrasound, Investigative Radiology 6:500–505 (1972).

PHASE SHIFT COLLOIDS AS ULTRASOUND CONTRAST AGENTS

This is a divisional of application Ser. No. 08/148,284, filed Nov. 8, 1993 U.S. Pat. No. 5,595,723, which is a continuation-in-part of application Ser. No. 08/008,172, filed Jan. 25, 1993 U.S. Pat. No. 5,558,855.

FIELD OF THE INVENTION

The present invention is directed to contrast agents for biomedical use comprising aqueous colloidal dispersions. More specifically, the present invention is directed to liquid in liquid emulsions in which the dispersed liquid undergoes a temperature or pressure activated phase shift from a dispersed liquid to a dispersed gaseous form which is efficient in reflecting ultrasound energy in a manner which is diagnostically useful.

BACKGROUND OF THE INVENTION

Various contrast agents for use with diagnostic ultrasound, including echocardiography, have been described. A review of the subject is found in Ophir and Parker, *Ultrasound in Med. & Biol.* (1989), 15:319–333. The acoustic backscatter arising from these agents, the property typically associated with the contrast effect, can be attributed to unique properties which they possess as solids, liquids or gases. While solids and liquids reflect sound to a similar degree, gases are known to be more efficient and are the preferred media for the development of ultrasound contrast agents.

Known liquid agents for ultrasound include emulsions and aqueous solutions. About these the authors of the above review stated, "the idea of using liquid emulsions of certain lipids in aqueous vehicles was tested by Fink et al. (1985). Unfortunately, no enhancement of backscatter was observable in these experiments."

Known solid agents include collagen microspheres. However, the poor acoustic backscatter of the solid-liquid interface prevents their wide spread use.

Known gaseous agents include microbubbles stabilized by the addition of various amphiphilic materials to the aqueous media, by materials that increase viscosity, and gaseous precursors, either as solid particles or liposomes. However, the liposomes can only contain water soluble gases and are thus limited in the stability of the microbubbles they can form, since one of the characteristic physical properties of many of the chemicals which form especially stable microbubbles is immiscibility in water. The solid particles must be reconstituted immediately before use, requiring extensive preparation, and must be used quickly, since the microbubbles disappear soon after the particles have completely dissolved. My own prior U.S. patent application Ser. No. 07/761,311 is directed to methods of determining the relative usefulness of gases as ultrasound contrast agents, and identifies particularly useful gases for that purpose.

One study has been identified which used the injection of a liquid which boils at a temperature below the boiling point of the organism under study to enhance the ultrasound Doppler signal (Ziskin M. C., Bonakdarpour A., Weinstein D. P., Lynch P. R.: *Contrast Agents For Diagnostic Ultrasound.* Investigative Radiology 7:500–505, 1972). In this study a number of solutions or liquids were injected intraarterially into dogs and the Doppler signal detected five cm below the injection site. This study reported that, "ether, which produced the greatest contrast effect of any agent that we tried, is a liquid which boils vigorously at body temperature and therefore acts as a very active source of bubbles." The report further stated that "ether, however, is a toxic substance when injected in large amounts. Injections of 20 mL proved fatal in our experiments." This paper does not discuss methods of stabilizing any materials suitable for later use as ultrasound agents. Non-colloidal ether is too toxic for intravenous administration, where the greatest need for a useful contrast agent exists.

The biocompatability of emulsions which include fluorocarbons is a serious safety concern. For example, Clark et al. (Clark L. C., Becattini F., Kaplan S.: Can fluorocarbon emulsions be used as artificial blood? Triangle 11:115–122, 1972) state, in speaking about the choice of fluorocarbon, "their vapor pressures range from zero to about 640 torr. Those with vapor pressures over 400 torr, of course, cannot be used because they would boil when infused in the blood stream." Later in the same article they state, "If a fluorocarbon with a vapor pressure of over 50 torr is given intravenously, death results in a few hours, and when the chest is opened, the lungs do not collapse." The same author, L. C. Clark, reports a similar conclusion exactly twenty years later, "If practical methods cannot be found to prevent or counteract HNCL (hyperinflated non-collapsible lungs), and if HNCL occurs in other species, then only fluorocarbons boiling above 150° C. can be considered safe," Clark C. L., Hoffmann R. E., Davis S. L.: Response of the rabbit lung as a criterion of safety for fluorocarbon breathing and blood substitutes, Biomat., Art. Cells & immob. Biotech., 20:1085–1099, 1992.

The stability of liquid-liquid emulsions presents another problem. A body of knowledge surrounds the stability of emulsions and the ability to predict stability from solubility; this theory is called the Ostwald ripening theory (Kabalnov A. S., Shchukin E. D.; *Ostwald Ripening Theory: Applications To Fluorocarbon Emulsion Stability*, Advances in Colloid and Interface Science, 38:69–97, 1992). This paper states, simply, that the more soluble is the dispersed phase liquid of an emulsion in the continuous phase, the less stable is the emulsion. These same authors tested the stability of a dodecafluoropentane emulsion at 25° C. (Kabalnov A. S., Makarov K. N., Shcherbakova O. V.: Solubility of fluorocarbons in water as a key parameter determining fluorocarbon emulsion stability. J Fluorine Chemistry 50:271–284, 1990). They determined that their emulsion had an Ostwald ripening rate of $1.4 \times 10^{-18}$ cm$^3$/s. Converting this rate constant into useful terms shows that Kabalnow et al's dodecafluoropentane emulsion, which had an initial size of 211 nm, would experience a particle mean diameter growth rate of 11 nm/sec or 660 nm/minute. At this rate of particle growth, such an emulsion would have a shelf life of less than a minute, and therefore be unworkable as a commercial product.

Thus, there is a need for an effective ultrasound contrast composition with extended shelf life, which is relatively easy to manufacture, which is biocompatible and convenient to use.

SUMMARY OF THE INVENTION

In order to meet these needs, the present invention is directed to stable colloidal dispersions of the liquid-in-liquid type. The colloids are ideally composed of a liquid dispersed phase which has a boiling point below the body temperature of the organism on which an ultrasound contrast study is desired, typically about 37°–40° C. These emulsions are preferably composed of a dispersed phase liquid which has a boiling point between −20° and 37° C.

Preferably the liquid dispersed phase is selected from the group of chemicals consisting of aliphatic hydrocarbons, organic halides or ethers, or combinations thereof, which have six or fewer carbon atoms and an upper limit of molecular weight of about 300. Among organic halides, the fluorine-containing chemicals are preferred, since they form stable emulsions and are relatively non-toxic. Especially preferred are n-pentane, isopentane, neopentane, cyclopentane, butane, cyclobutane, decafluorobutane, dodecafluoropentane, dodecafluoroneopentane, perfluorocyclopentane and mixtures thereof. Preferably, the colloidal dispersion contains the dispersed phase at a concentration of 0.05 to 5.0% w/v. Optimally, the concentration range is 0.5 to 3.5% w/v.

The colloidal dispersion can be stabilized by the addition of various amphiphilic materials, including anionic, nonionic, cationic, and zwitterionic surfactants, which typically lower the interfacial tension between the dispersed liquid and water to below 26 dynes/cm. Optimally, these materials are nonionic, synthetic surfactant mixtures, containing a fluorine-containing surfactant, such as the Zonyl brand series and a polyoxypropylene-polyoxyethylene glycol nonionic block copolymer.

The liquid continuous phase of the colloidal dispersion comprises an aqueous medium. This medium can contain various additives to assist in stabilizing the dispersed phase or in rendering the formulation biocompatible. Acceptable additives include acidifying agents, alkalizing agents, antimicrobial preservatives, antioxidants, buffering agents, chelating agents, suspending and/or viscosity-increasing agents, including triodobenzene derivatives, such as iohexol or iopamidol, and tonicity agents. Preferably, agents to control the pH, tonicity, and increase viscosity are included. Optimally, a tonicity of at least 250 mOsm is achieved with an agent which also increases viscosity, such as sorbitol or sucrose.

The colloidal dispersions are typically formed by comminuting a suspension of the dispersed phase in the continuous phase by the application of mechanical, manual, or acoustic energy. Condensation of the dispersed phase into the continuous phase is also acceptable. The preferred mode is to use high pressure comminution.

DETAILED DESCRIPTION OF THE INVENTION

The invention relates to agents that enhance the contrast in an ultrasound image generated for use in medical and veterinary diagnosis. These agents are comprised of biocompatible colloidal dispersions in which the dispersed phase is a liquid under the conditions of the manufacturing process and which undergoes a phase shift to become a dispersed gas or kugelschaum at or about the time of administration to the organism under study.

In order to provide a clear and consistent understanding of the present invention and claims, including the scope given to such terms, the following definitions relating to the invention are provided:

Colloidal Dispersion: A system having at least one substance as a liquid or gas (the dispersed phase) which is immiscible and finely divided and distributed evenly throughout at least one second substance which forms the dispersion medium or continuous liquid phase.

Biocompatible: Capable of performing functions within or upon a living organism in an acceptable manner, without undue toxicity or physiological or pharmacological effects.

Liquid: The state of matter in which a substance or substances exhibit(s) a characteristic readiness to flow, little or no tendency to disperse, and relatively high incompressibility.

Gas: The state of matter of a substance or substances which is distinguished from the solid or liquid states by very low density and viscosity, relatively great expansion and contraction with changes in temperature and pressure, and the spontaneous tendency to become distributed uniformly throughout any container.

Phase Shift: A change of state between liquid and gas due to changes in temperature and/or pressure.

Kugelschaum: One of the two forms of foams in the classification of Manegold (Manegold, E. "Schaum, Strassenbau, Chemie und technik." Heidelberg, 1953, which is incorporated herein by reference). Specifically, the kugelschaum or spherical foam, consists of widely separated spherical bubbles and is distinct from the polyederschaum or polyhedral foams, which consist of bubbles that are nearly polyhedral in shape, having narrow lamellar films of very low curvature separating the dispersed phase.

Low Boiling Liquid: A liquid with a boiling point, under standard pressure conditions, below 37° C. Low boiling liquids useful in the invention include, but are not limited to, those selected from the chemical group: Isobutane; Ethane, 1-chloro-1,1,2,2-tetrafluoro; Isobutylene; Dimethyl amine, hexafluoro; 1-Butene; 1,3-Butadiene; Cyclobutane, octafluoro; Propylene, 3-fluoro; Dimethyloxonium chloride; Methanesulfenylchloride, trifluoro; n-Butane; Propane, 2,2-difluoro; Ethane, nitro-pentafluoro; 2-Butene {trans}; 1,2-Benzanthracene, 4-methyl; Propane, 1,1,1,2,2,3-hexafluoro; Azomethane; Phthalic acid, tetrachloro; Trimethyl amine; Cyclobutene, perfluoro; Ethane, 1,1-dichloro-1,2,2,2-tetrafluoro; 2-Butene {cis}; Butane, decafluoro; Acetylene-bromo; 1-Butene, perfluoro; Benzoyl chloride, pentachloro; Vinyl acetylene; 1,3-Butadiene, hexafluoro; Methanethiol; Carbon suboxide; Ethane, 2-chloro-1,1,1-trifluoro; Dimethyl amine; 1-Butyne; Methane, dichloro-fluoro; Neopentane; Neopentane, perfluoro; Butadiyne; 1,2-Butadiene; Ethyl methyl ether; 1,3-Butadiene, 2-fluoro; Crotononitrile; Cyclobutane; Isobutane, 1,2-epoxy-3-chloro; Methyl vinyl ether; Ethane, Chloro; Diazoethane, 1,1,1-trifluoro; Methane, disilano; Ethyl amine; 2,3-Dimethyl-2-norbornano; Borine, trimethyl; 1-Butene, 3-methyl; Cyclopropane, 1,1-dimethyl; Acetaldehyde; Acetyl flouride; Borine, dimethyl, methoxy; Ethylene, 1,2-dichloro-1,2-difluoro; Methane, difluoro-iodo; Propylene, 2-chloro; Carvone- {d}; Methane, trichlorofluoro; 1,3-Dioxolane-2-one, 4-methyl; Methane, dibromo difluoro; Methane, chloro difluoro nitro; 2-Pentanone, 4-amino-4-methyl; Propane, heptafluoro-1-nitro; Hydrocyanic acid; 3-Butene-2-one, 4-phenyl {trans}; 1,5-Heptadiyne; 1,4-Pentadiene; 2-Butyne; Butane, 2-methyl; 2-Methyl butane; Cyclopropane, 1,2-dimethyl {trans, dl}; Toluene, 2,4-diamino; 1-Butyne, 3-methyl; 1-Pentene; Pentane, perfluoro; 1-Pentene, 3-bromo; Ethane, 1,2-difluoro; 1-Butene, 2-methyl; Formic acid, methyl ester; Methane sulfonyl chloride, trifluoro; Diaziridine, 3-ethyl-3-methyl; Ethane, 1,1-dichloro-1-fluoro; Propane, 2-amino; Butane, 1-fluoro; Methyl isopropyl ether; Propylene, 1-chloro; Butyraldehyde, 2-bromo; bis-(imethyl phosphino) amine; 1,3-Butadiene, 2-methyl; 1-Butene-3-yne, 2-methyl; Isoprene;

Propane, 1,2-epoxy; Cyclopropane, ethyl; Ethyl ether; Dimethyl disulfide, hexafluoro; Propane, 2-chloro; Ethyl hypochlorite; Methane, bromo-chloro-fluoro; Piperidine, 2,3,6-trimethyl; n-Pentane; Cyclobutane, methyl; 2-Pentene {trans}; Ethyl methyl amine; 2-Pentene {cis}; Cyclopropane, 1,2-dimethyl {cis}; Ethylene, 1,1-dichloro; Hydrazoic acid; Methyl sulfide; Propylene, 1-chloro-{trans}; Ethylene, 1,1-dichloro-2-fluoro; 2-Butene, perfluoro; Ethyl nitrite; Methane, bromo fluoro; Cyclopentene, 3-chloro; 1-Nonene-3-yne; Cyclopropane, 1,2-dimethyl {trans, 1}; 1-Pentene, perfluoro; Styrene, 3-fluoro; Acetylene-diido; 1,3-Butadiene, 1,2,3-trichloro; Methane, chloro dinitro; Ethyl vinyl ether; Dimethyl ethyl amine; and 1,2,3-Nonadecane tricarboxylic acid.

High Vapor Pressure Chemical: A chemical with a sufficiently high vapor pressure that colloidal dispersions of the chemical as a liquid contain, at the body temperature of an organism undergoing an ultrasound examination, a sufficient quantity of the chemical as a gaseous dispersion to provide a diagnostically useful alteration in the ultrasound data obtained during an examination. High vapor pressure chemicals include low boiling liquids, a preferred embodiment of the present invention. Chemicals with vapor pressures at ambient temperature of above 20 Torr (typically having boiling points below 135° C.) are another preferred embodiment. The latter class of chemicals which are useful in this invention include, but are not limited to: perfluorinated n-alkanes, cycloalkanes, and branched alkyl compounds containing up to nine carbons (nonane; B.P. 125° C.); alkyl hydrocarbons containing up to ten carbons, such as n-decane; ethers, other organic halides, and alcohols.

Aliphatic Hydrocarbons: The group of alkane, alkene, alkyne, cycloalkane, and cycloalkene organic compounds. Only the members of the group with six or fewer carbon atoms have boiling points below 37° C. and are thus capable of undergoing a liquid to gas phase transition after administration to a subject. Aliphatic hydrocarbons useful in the invention include, but are not limited to, those selected from the chemical group: Isobutane; Isobutylene; 1-Butene; 1,3-Butadiene; n-Butane; 2-Butene {trans}; 2-Butene {cis}; Vinyl acetylene; 1-Butyne; Neopentane; Butadiyne; 1,2-Butadiene; Cyclobutane; 1-Butene, 3-methyl; Cyclopropane, 1,1-dimethyl; 1,3-Dioxolane-2-one, 4-methyl; 3-Butene-2-one, 4-phenyl {trans}; 1,5-Heptadiyne; 1,4-Pentadiene; 2-Butyne; Butane, 2-methyl; Cyclopropane, 1,2-dimethyl {trans, dl}; 1-Butyne, 3-methyl; 1-Pentene; 1-Butene, 2-methyl; 1,3-Butadiene, 2-methyl; 1-Butene-3-yne, 2-methyl; Isoprene; Cyclopropane, ethyl; n-Pentane; Cyclobutane, methyl; 2-Pentene {trans}; 2-Pentene {cis}; Cyclopropane, 1,2-dimethyl {cis}; and 1-Nonene-3-yne.

Organic Halides: The group of compounds containing at least one carbon or sulfur atom and at least one halogen atom, i.e., chlorine, bromine, fluorine, or iodine. Only the members of the group with six or fewer carbon atoms are capable of undergoing a phase transition upon administration to an organism with a body temperature of 37° C. Organic halides useful in the invention include, but are not limited to: Methane, tetrafluoro; Methane, nitrosotrifluoro; Methane, trifluoro; Methane, chlorotrifluoro; Ethane, hexafluoro; Ethane, perfluoro; Methane, fluoro; Ethylene, tetrafluoro; Sulfur hexafluoride; Trifluoroacetonitrile; Methane, bromotrifluoro; Methane, difluoro; Propyne, 3,3,3-trifluoro; Ethane, 1,1,1-trifluoro; Ethane, nitrosopentafluoro; Methane, chloro-difluoro; Allene, tetrafluoro; Ethane, 1-chloro-1,1,2,2,2-pentafluoro; Ethane, chloropentafluoro; Ethane, fluoro; Dimethylamine, perfluoro; Propane, perfluoro; Ethyl amine, perfluoro; Trifluoromethyl peroxide; Azomethane, hexafluoro; Methane, nitrotrifluoro; Methane, dichlorodifluoro; Propylene, perfluoro; Acetone, hexafluoro; Ethane, 1,1,1,2-tetrafluoro; Ethylene, 1-chloro-1,2,2-trifluoro; Ethylene, chlorotrifluoro; Ethane, 1,1-difluoro; 2-Butyne, perfluoro; Methane, iodotrifluoro; Trifluoromethyl sulfide; Methane sulfonyl fluoride, trifluoro; Methane, (pentafluorothio)trifluoro; Methane, bromodifluoronitroso; Propane, heptafluoro-1-nitroso; Ethane, 1-chloro-1,1,2,2-tetrafluoro; Cyclobutane, octafluoro; Propylene, 3-fluoro; Methanesulfenylchloride, trifluoro; Propane, 2,2-difluoro; Ethane, nitropentafluoro; Propane, 1,1,1,2,2,3-hexafluoro; Cyclobutene, perfluoro; Ethane, 1,1-dichloro-1,2,2,2-tetrafluoro; Butane, decafluoro; 1-Butene, perfluoro; 1,3-Butadiene, hexafluoro; Ethane, 2-chloro-1,1,1-trifluoro; Methane, dichloro-fluoro; 1,3-Butadiene, 2-fluoro; Diazoethane, 1,1,1-trifluoro; Acetyl flouride; Ethylene, 1,2-dichloro-1,2-difluoro; Methane, difluoroiodo; Methane, trichlorofluoro; Methane, dibromodifluoro; Methane, chlorodifluoro nitro; Propane, heptafluoro-1-nitro; Pentane, perfluoro; Neopentane, perfluoro; Ethane, 1,2-difluoro; Methane sulfonylchloride, trifluoro; Ethane, 1,1-dichloro-1-fluoro; Butane, 1-fluoro; Dimethyl disulfide, hexafluoro; Methane, bromochlorofluoro; Ethylene, 1,1-dichloro-2-fluoro; 2-Butene, perfluoro; Methane, bromofluoro; 1-Pentene, perfluoro; Styrene, 3-fluoro; Boron fluoride dihydrate; Butyne, 2-chloro-1,1,1,4,4,4-hexafluoro; Ethane, 1,1,2,2-tetrafluoro; Ethane, 1,1,2-trichloro-1,2,2-trifluoro; Ethane, 1,2-dichloro-1,1,2,2-tetrafluoro; Ethane, 2-chloro, 1,1-difluoro; Ethane, dichlorotrifluoro; Ethylene, 1,2-difluoro; Ethylene, dichlorodifluoro; Methane, chlorofluoro; and Propyl, 1,1,1,2,3,3-hexafluoro-2,3-difluoro.

Ethers: The class of organic compounds in which two hydrocarbon groups or derivatives thereof are linked by an oxygen atom. For the purposes of the present invention the following are examples of some, but not necessarily all, ethers which can be used: methyl ether, ethyl methyl ether, methyl vinyl ether, methyl isopropyl ether, 1,2-epoxypropyl ether, diethyl ether, ethyl vinyl ether, and vinyl ether.

Fluorine-Containing Compounds: A compound containing at least one fluorine atom. Useful fluorine-containing compounds are listed as above listed organic halides.

The colloidal dispersions of the invention can be emulsions or microemulsions.

Emulsion: A colloidal dispersion of one immiscible liquid dispersed in another liquid in the form of droplets, whose diameter, in general, are between 100 and 3000 nm and which is typically optically opaque, unless the dispersed and continuous phases are refractive index matched. Such systems possess a limited stability, generally defined by the application or relevant reference system, which may be enhanced by the addition of amphiphilic materials or viscosity enhancers.

Microemulsion: A stable liquid monophasic and optically isotropic colloidal dispersion of water and water-immiscible liquids stabilized by amphiphilic materials in which the dispersions have appreciable light scattering properties (meaning they can appear optically clear or milky but are reddish or yellowish if observed by transmitted light) and the diameters of the particles are, in general, between 5 and approximately 140 nm.

In a preferred embodiment of the present invention, the colloidal dispersion contains one or more amphiphilic materials to improve the stability of the formulation.

Amphiphilic Material: A substance which is strongly adsorbed at an interface and which normally produces a dramatic reduction in the interfacial tension with small changes in the bulk phase concentration. Examples include synthetic surfactants, naturally occurring materials such as biocompatible proteins, lipids, sterols, alginates, cellulose derivatives, and finely divided organic or inorganic particulate solids.

Organic Particulate Solids: include sugars, proteins, amino acids, lipids, nucleic acids, and others.

Inorganic Particulate Solids: include aluminas, carbonates, bicarbonates, silicates, aluminasilicates, phosphates, and others.

Interface: The region or boundary of the physical world that lies between two distinct and identifiable phases of matter, herein limited to liquid-liquid, liquid-solid, solid-gas, and liquid-gas.

Interfacial Tension: The force per length which exists at the interface between two distinct and identifiable phases of matter.

Stability: The time lapse from initial preparation and packaging during which a colloidal dispersion continues to fulfill all chemical and physical specifications with respect to identity, strength, quality, and purity which have been established according to the principles of Good Manufacturing Practice, as set forth by appropriate governmental regulatory bodies.

Surfactants: The group of amphiphilic materials which are manufactured by chemical processes or purified from natural sources or processes. These can be anionic, cationic, nonionic, and zwitterionic, and include the following distinct chemical groups:

Group 1: Acetamide Monoethanolamine (Mea), Acetylenic Diol, Acetylenic Diol Blend, Proprietary, Alcohol Alkoxylates, Alcohol And Alcohol Ether Sulfates, Alcohol-Ethoxylated-Propoxylated Surfactant Defoamer, Alcohol Ethoxysulfates, Alcohol, Oxyalkylated, Alcohol, Polyoxyethaylated Synthetic, Alcohols, Alkoxylated Linear, Alcohols, Detergent, Alcohols, Ethoxylated, Alcohols, Low-Foam Alkoxylated, Alcohol Sulfates, Aliphatic Alcohols, Ethoxylated Branched, Aliphatic Diamines, Aliphatic Ethoxylate, Linear, Aliphatic Nonionics, Alkanolamides, Alkoxylated Linear Alcohol Carboxylic, Acid Sodium Salts, Alkoxypolyalkoxyethanol, Alkyl Acid Phosphates, Alkyl Alkoxylate, Fluorinated, Alkylamine, Polyoxyethylated, Alkyl Amphoteric, Fluorinated, Alkylaryl Polyether, Alkylaryl Polyethoxylate-Sodium Salt Of Alkylsulfonatedalkylate Blend, Alkylaryl Polyoxyethylene Ether, Alkylaryl-Polyoxyethylene-Glycol, Phosphate Ester Surfactants, Solubilizers, Alkylaryl Polyoxyethylene Glycols, Alkylaryl Sulfonate;

Group 2: Alkylate Sulfonate, Linear, Alkylbenzenes, Alkyl Betaine, Alkyl Esters, Fluorinated, Alkyl Ether Sulfates, Alkyl Ethoxylate, Alkyl Imidazolines, Alkylolamides, Fatty Acid, Alkylolamides, Methyl Cocoate, Alkylphenol Alkoxylates, Alkylphenol Condensate, Ethoxylated, Alkylphenols, Ethoxylated, Alkylphenols, Polyoxyethylated, Alkyl Polyglycosides, Alkyl Quaternary, Fluorinated, Alkyl Sulfate, Alkyl Sulfate, Lauryl Alcohol, Amidoamine Methosulfate, Amidopropylamine Oxide, Amine Condensate, Amine Oxides, Amines, Primary, Ethoxylated, Amines, Tertiary, Ammonium Cumene Sulfonate, Ammonium Ether Sulfate, Ammonium Laureth Sulfate, Ammonium Lauryl Sulfate, Ammonium Lauryl Sulfosuccinate, Ammonium Xylene Sulfonate, Amphoterics; Group 3: Amphoteric Salts, Anionic And Nonionic Surfactants, Anionic-Nonionic Blend Emulsifiers, Anionic-Nonionic Blends, Aromatic And Aliphatic Phosphate Esters, Avocadamine Dea And Avocado Oil, Betaines, Betaines, Amphoteric, Calcium Stearoyl 2-Lactylate, Capric Diethanolamide, Carboxylated Alkyl, Aryl-Alkyl Polyethoxylates, Castor Glycerides, Polyoxyethylated, Hydrogenated, Castor Oil, Ethoxylated, Castor Oil, Ethoxylated, Hydrogenated, Castor Oil, Refined Castor Oil, Sulfonated, Cationic Surfactant, Cetyl Acetate And Acetylated Lanolin Alcohol, Cocamide, Diethanolamine (Dea), Cocamide Monoethanolamine (Mea), Cocamidopropyl Amine Oxide, Cocamidopropyl Betaine, Cocamidopropyl Dimethylamine, Cocamphocarboxyglycinate, Cocoamine, Ethoxylated, Cocoamine Oxide, Cocoamine, Polyoxyethylated;

Group 4: Cocodiethanolamide, Coconut Acid Ester Of Sodium Isethionate, Coconut Amide Nonionics, Coconut Diethanolamide (68603-42-9), Coconut Monoethanolamide, Coconut Oil Diethanolamine Condensate, Cocoyl Imidazoline, Cocoyl Sarcosine, Cyclodextrins, Alpha, Beta, Gamma, Deceth-4 Phosphate, Decyl Alcohol, Ethoxylated, Decyl-Diphenyl Oxide Disulfonic Acid, Defoamer Blend, Demulsifiers (Emulsion Breakers), Diacetyltartaric Acid Esters Of Monoglycerides, Dialkyl(C12 C18) Dimethylammonium Chloride, Dicarboxylcocoimidazoline Compound, Diethanolamines, 2:1, Diethanolamine Lauryl Sulfate, Diethylene Glycol Monosterate, 3,5-Dimethyl-1-Hexyn-3-O1, 3,6-Dimethyl-4-Octyne-3,6-Diol, Dimethyl Tertiary Amines, Dinonylphenols; Group 5: Polyoxyethylated, Disodium Cocamido-Ethanolamine Sulfosuccinate (Mea), Disodium Cocamido Iso-Propanolamine Sulfosuccinate (Mipa), Disodium Ethoxylated Alcohol Half Ester Of Sulfosuccinic Acid, Disodium Ethoxylated Nonylphenol Half Ester Of Sulfosuccinic Acid, Disodium Lauramido-Ethanolamine Sulfosuccinate (Mea), Disodium Laureth Sulfosuccinate, Disodium Oleamido-Ethanolamine Sulfosuccinate(Mea), Disodium Oleamido-polyethyleneglycol-2-Sulfosuccinate, Disodium Oleamido-Iso-Propanolamine Sulfosuccinate (Mipa), Disodium Ricinoleamidoethanolamine Sulfosuccinate (Mea), Disodium Undecylenamido-ethanolamine Sulfosccinate (Mea), Dispersing Agents, Distearyldimethylammonium Chloride, Ditallowdimethylammonium Chloride, Dodecylbenzenesulfonic Acid;

Group 6: Dodecyldiphenylether Disulfonic Acid, Dodecyldiphenyl Oxide Disulfonic Acid, Dodecyl Diphenyl Oxide Sulfonate, Dodecylphenols, Emulsified Surfactant Defoamer, Emulsifiers, Emulsion Stabilizers, Esters, Ethanol-2-Phenolxy, Ether Sulfate, Ethoxylate, Complex, Ethoxylated Acetylenic Diol, Ethoxylated Alcohol Blends, Ethoxylated Alcohol Defoamer, Ethoxylated Derivatised Phenols, Ethoxylated-Emulsified Surfactant Defoamer, Ethoxylated Esters, Ethoxylated Fatty Acid Esters, Ethoxylated Fatty Alcohol Ethoxylated Lanolin Alcohols, Ethoxylated Polyoxypropylene Glycols, Ethoxylated-Propoxylated Block Copolymers Ethoxylated-Propoxylated Block Polymers, Ethoxylated-Propoxylated Surfactant Defoamer, Ethoxylated Sulfonate, Ethoxylated Surfactant Antifoam, Ethoxylated Surfactant Blend Defoamer, Ethoxylated Surfactant Defoamer;

Group 7: Ethoxylates, Nonionic, Ethoxylate Sulfate, Ammonium Salt, Ethoxylate Sulfate, Lauryl Alcohol, Ethylene Glycol Distearate, Ethylene Glycol Monostearate, Ethylene Oxide Adduct, Ethylene Oxide Condensate, Ethylene Oxide-Nonylphenol Adduct, Fatty Acid Alkoxylates, Fatty Acids, Polyoxyethylated, Fatty Alcohol-Ethylene Oxide Condensates, Fatty Alcohol Nonionic, Fatty Alcohol, Polyoxyethylated, Fatty Amides And Bisamides, Fatty Amine Alkoxylates, Fatty Diethanolamides, Fluorinated Surfactants, Fluoroalkyl Carboxylates, Fluorocarbons, Fluorosurfactants, Foamers, Glycerol Monooleate, Glycerol Monostearate, Hexadecyl Diphenylether Disulfonic Acid, Hydrotropes, Xylene, Imidazolines, Isoalcohol, Alkoxylated, Isopropylamine;

Group 8: Dodecyclbenzene Sulfonate, Isostearyl Alcohol, Alkoxylated, Isostearyl Lactate, Jojoba Oil Derivatives, Kerosene (Deodorized) Organic Defoamer, Lactamide Ethanolamine (Mea), Lanolin, Ethoxylated, Lauramide Diethanolamine (Dea), Lauramide Ethanolamine (Mea), Lauramide Nonionics, Lauramidopropyl Amine Oxide, Lauramidopropyl Betaine, Lauramidopropyl Dimethylamine, Lauramine Oxide, Lauric Acid, Ethoxylated, Lauric Acid Monoisopropanolamide, Lauric Diethanolamide, Lauric-Myristic Diethanolamide, Lauroyl Sarcosine, Lauryl Alcohol, Ethoxylated, Lauryl Monoethanolamide, Lauryl Polyglucose, Ligninamine, Lignin (Sulfonated), Sodium Salts;

Group 9: Linear Alcohols, Ethoxylated, Linoleic Diethanolamide, Methylbis- (Hydr.Tallowamidoethyl)-2-Hydroxyethylammonium Methyl Sulfate, Methylbis (Tallowamidoethyl)-2-Hydroxypropyl Ammonium Methyl Sulfate, Methyl-1-Oleylanidoethyl-2-Olelimidazolinium Methyl Sulfate, Methyl-1-Tallowamidoethyl-2-Tallowimidazolinium Methyl Sulfate, Mineral Seal Oil-Based Defoamer, Monocarboxylcocoimidazoline Compound, Monodiglycerides, Monoglyceride Citrate, Monoglycerides, Ethoxylated, Naphthalene-Formaldehyde Condensate (Sulfonated), Sodium Salt, Nonionic Surfactant Nonyldiphenyl Ether Disulfonic Acid, Nonylphenol Ethoxylate, Nonylphenol Nonionics, Nonylphenols, Polyoxyethylated;

Group 10: Nonylphenoxypoly(Ethyleneoxy) Ethanol (Sulfated), Ammonium Salt, Octylphenol Ethoxylate, Octylphenols, Polyoxyethylated, Octyl Salicylate, Oleamide Diethanolamini (Dea), Oleamidopropyl Dimethylamine, Oleic Acid, Ethoxylated Oleic Diethanolamide, N-Oleoylsarcosine, Oleyl Alcohol Phosphate Ester, Oleyl Alcohol, Polyoxyethylated, Oleylamine, Ethoxylated, Organic Phosphate Esters, Free Acids Of, Organic Salt, Organic-Silicone Blend, Antifoam, Organic-Silicone Defoamer, Oxazolines, Paper Additives, Peg-15 Cocamine Phosphate Oleate, Perfluoroalkyl Sulfonates, Phosphate Acid Esters, Aliphatic Base, Phosphate Acid Ester, Aromatic Base, Phosphate Acid Esters, Aromatic Hydrophobic Base, Phosphate Acid Esters, Fatty Alcohol, Phosphate Acid Esters, Linear Alcohol, Phosphated Alcohol Ethoxylate, Phosphate Ester, Aliphatic Hydrophobic Base;

Group 11: Phosphate Ester-Free Acids, Phosphate Ester, Partial Sodium Salt, Phosphate Esters, Phthalic Glycerol Alkyd Resin, Modified, Polyacrylic Acid, Polyalkylene Oxide, Polyether, Alkoxylated, Polyether, Block Polymer, Polyethers, Polyethoxylated Amines, Polyethoxylated Fatty Acids, Polyethylene Emulsions, Polyethylene Glycol Dioleates, Polyethylene Glycol Ditallate, Polyethylene Glycol Esters, Polyethylene Glycol Monolaurate, Polyethylene Glycol Monooleate, Polyglycerol Esters, Polyoxyethylene Caster Oil, Polyoxyethylene Cocoamine, Polyoxyethylene Oleic Acid, Polyoxyethylene Stearic Acid, polyoxyethylene Tallowamine, Polypropylene Glycol Distallate;

Group 12: Polypropylene Glycol Ester, Polysodium Vinylsulfonate, Potassium And Sodium Soaps, Potassium Cocoates, Potassium Toluenesulfonate, Propoxylated Alcohol, Propoxylated Polyoxyethylene Glycols, Pyridine-3-Sulfonic Acid, Quaterinaries, Quaternary Alkylamines, Quaternary Ammonoim Compounds, Quaternary Ammonium Salts, Quaternary Biocides, Ricinoleamide Diethanolamine (Dea), Ricinoleic Diethanolamide, Silicone Antifoams, Silicone Coatings, Silicone Defoamers, Silicone Emulsions, Silicone Fluids, Silicone-Glycol Copolymers, Sodium Alkylarylsulfonate Sodium Alkylnaphthalenesulfonate, Sodium Bistridecyl Sulfosuccinate, Sodium Butoxyethoxy Acetate, Sodium Capryl Lactylate, Sodium N-Cocoyl-N-Methyltaurate;

Group 13: Sodium Cocoylsarcosinate, Sodium Cumenesulfonate, Sodium Decyldiphenyl Ether Sulfonate, Sodium Diamyl Sulfosuccinate, Sodium Dibutyl Sulfosuccinate, Sodium Dicarboxyethylcoco Phosphoethyl Imidazoline, Sodium Dicyclohexyl Sulfosuccinate, Sodium Dihexyl Sulfosuccinate, Sodium Diisobutyl Sulfosuccinate, Sodium Dioctylsulfosuccinate, Sodium Dioctylsulfosuccinate And Mineral Spirits, Sodium Dioctylsulfosuccinate And Propylene Glycol, Sodium Dodecylbenzenesulfonates, Sodium Dodecyldiphenyl Ether Sulfonate, Sodium 2-Ethylhexyl Sulfate, Sodium Isodecyl Sulfosuccinate, Sodium Isostearoyl Lactylate, Sodium Laureth Sulfate, Sodium Lauroyl Lactylate, Sodium Lauroylsarcosinate, Sodium Lauryl Sulfate, Sodium Lauryl Sulfoacetate, Sodium N-Methyl-N-Oleoyltaurate, Sodium Naphthalene Sulfonate, Sodium 1-Octane Sulfonate, Sodium C14–16 Olefin Sulfonates, Sodium Polyacrylate, Sodium Stearoyl Lactylate, Sodium Tetradecyl Sulfate, Sodium Toluenesulfonate, Sodium Toluene-Xylenesulfonate, Sodium Vinylsulfonate, Sodium Xylene Sulfonate, Sorbitan And Ethoxylated Sorbitan Esters, Sorbitan Oleate, Sorbitan Stearate, Soya Amine;

Group 14: Polyoxyethylated, Soyamide Diethanolamine (Dea), Stearalkonium Chloride, Iso-Stearamidopropyl Bentaine, Stearamidopropyl Dimethylamine, Stearamidopropyl Pg-Dimonium Chloride Phosphate, Stearic Acid Diethanolamide, Stearic Acid, Ethoxylated; and Group 15: Stearic Acid Monoethanolamide, Stearic Imidazoline, Stearylamine, Ethoxylated, Succinimides, Basic, Sucrose Esters, Sulfate Ester, Sulfates And Ether Sulfates, Sulfobetaines, Sulfonates, Sulfonates, Dodecylbenzene, Sulfonic Acid, Linear Alkyl(C-12) Benzene, Sulfosuccinamates, Sulfosuccinate Esters, Sulfosuccinates, Surfactant, Oil Defoamer, Surfactant Solution Defoamer, Surfactants, Low-Foaming, Surfactants, Soluble-Oil-Base, Polyoxyethylated Tall Oil Fatty Acid, Ethoxylated Tall Oil Fatty Acids, Tall Oil Imidazoline, Ethoxylated Tallowamine, Polyoxyethylated Tallowamine, Dihydrogenated Tallowdimethylammonium Chloride, Dihydrogenated Tallowdimethylammonium Methyl Sulfate, Tetrahydroxy-propylethylenediamene, Tert-Thioethoxylate, Toluenesulfonic Acid, Ethoxylated Tridecyl Alcohol, Tridecyloxypoly-(Ethyleneoxy)-Ethanol, Triethanolamine Lauroylsarcosinate, Triethanolamine Lauryl Sulfate, Triethanolamine Phosphate Ester, Trimethylnonyl Ether Of Polyethylene Glycol, Wetting Agents, Yucca Extract.

The continuous phase of the colloidal dispersion of the present invention is an aqueous medium.

Aqueous Medium: A water-containing liquid which can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, can be found in the *U.S. Pharmacopeia National Formulary,* 1990, pp, 1857–1859, which is incorporated herein by reference.

A preferred embodiment of the present invention includes the use of at least one amphiphilic material from the groups consisting of biocompatible proteins, fluorine-containing surfactants, polyoxypropylene-polyoxyethylene glycol nonionic block copolymers, and surfactants.

Polyoxypropylene-Polyoxyethylene Glycol Nonionic Block Copolymers: The surfactants which are available from BASF Performance Chemicals, Parsippany, New Jersey under the trade name Pluronic and which consists of the group of surfactants designated by the CTFA name of poloxamer 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403.

Fluorine-Containing Surfactant: A surfactant containing one or more fluorine molecules. Some but not necessarily all fluorine containing surfactants, useful in this invention can be selected from the group consisting of: telomer B containing fluorinated surfactants available from Du Pont, Wilmington, Del. under the Trade name of Zonyl (including Zonyl FSA, FSP, FSE, UR, FSJ, FSN, FSO, FSC, FSK, and TBS), the fluorochemical surfactants from 3M Industrial Chemical Products Division, St. Paul, Minn. under the trade name of Fluorad (including FC-95, FC-98, FC-143, FC-170C, FC-171, FC-430, FC-99, FC-100, FC-120, FC-129, FC-135, FC-431, FC-740), the perfluoroalkylpoly (oxyethylene) surfactants described by Mathis et al. (*J Am Chem Soc* 106, 6162–6171 (1984), incorporated herein by reference), the fluoroalkylthio-etherpoly(oxyethylene) surfactants described by Serratrice et al. (*J Chim Phys* 87, 1969–1980 (1990), incorporated herein by reference), he perfluoroalkylated polyhydroxylated surfactants of Zarif et al. (*J Am Oil Chem Soc* 66, 1515–1523 (1989), incorporated herein by reference), the fluorosurfactants available from Atochem North America, Philadelphia, Pa. under the trade name of Forafac.

Biocompatible Proteins: The group of proteins, regardless of source and whether obtained by extraction of animal, plant, or microbiological tissue or obtained from recombinant biotechnology, which is capable of performing its function of stabilizing the colloidal dispersions of the instant invention in an acceptable manner, without undue toxicity or physiological or pharmacological effects. Some acceptable biocompatible proteins can be selected from the group consisting of albumin, alpha-1-antitrypsin, alpha fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, hemoglobin, myoglobin, immunoglobulins, lactate dehydrogenase, lipase, lipoproteins, acid phosphatase, alkaline phosphatase, alpha-1-serum protein fraction, alpha-2 serum protein fraction, beta protein fraction, gamma protein fraction, gamma-glutamyl transferase, and other proteins.

A preferred process for manufacturing the colloidal dispersions of this disclosure is comminution. An alternative process for manufacturing is condensation.

Comminution: The process of forming a colloidal dispersion by mixing the liquid dispersed and continuous phases together and then causing a decrease in size of the particles of the dispersed phase from large particles to the size required, using mechanical energy generated by mixing manually, mechanically, or by the action of ultrasound. Appropriate mixing can be achieved in a Microfluidic's Model 110 Microfluidizer apparatus, as described in U.S. Pat. No. 4,533,254, incorporated herein by reference. An acceptable alternative is the Rannie High Pressure Laboratory Homogeniser, Model Mini-Lab, type 8.30H, or equivalent.

Condensation: The process of forming a colloidal dispersion by starting with the dispersed phase as a gas, placing it in contact with the liquid continuous phase and then causing an increase in size of the particles of the dispersed phase from a molecular ensemble to the size required, generally by inducing a phase change of the dispersed gas to a liquid by the action of changes in the system temperature, pressure, or both.

The invention will be better understood by way of the following examples:

EXAMPLE 1

The criticality that the low boiling liquid be present as a finely divided dispersion rather than as a neat liquid, as was described by Ziskin et al. (referenced above) was determined by measuring the acoustic backscatter of the two states.

Two solutions were prepared to simulate the administration to an organism of either a colloidal dispersion of a low boiling liquid or the liquid neat. These were scanned at 5.0 MHz with a Hewlett Packard Model 77020 ultrasound scanner and the images obtained recorded on Sony ES VHS tape. The analog images from the tape were then converted to a digital form using the software package Global Lab Image Software (Data Translation, Marlboro, Mass.). The gray scale intensity within a 4900 pixel (70×70 pixel-sized) region-of-interest was then measured before and after the injection of the colloidal dispersion of Example 19 or a quantity of neat dodecafluoropentane into a 1000 mL water beaker equilibrated at 37° C.

The measurements were performed on a gray scale of 2 to 254. The image intensity before injection of a 0.1 mL aliquot of the emulsion of Example 19 below (containing 3.4 micromoles of dodecafluoropentane) was 4.27. The injection of 0.1 mL of this emulsion produced a change of intensity to 236 five seconds post-injection and 182 fifty-two seconds post-injection.

The same experiment was performed with a 0.2 mL injection of neat dodecafluoropentane. This corresponds to 1111 micromoles of dodecafluoropentane, over 300-times the quantity in the experiment above. The image intensity before injection was 4.9; this increased to 7.7 five seconds post-injection and 5.0 fifty-two seconds post-injection.

A comparison of these two experiments (intensity/quantity) indicates that the colloidal dispersion is 27,000-times more effective at scattering the ultrasound beam than simply an administration of a liquid which also undergoes a liquid-to-gas phase transition.

EXAMPLE 2

The selection of an appropriate chemical for the liquid dispersed phase is governed, in part, by the body temperature of the organism to be studied by ultrasound. For example, since the body temperature of man is 37° C., liquids which undergo a liquid to gas phase transition, i.e., boil, at or below 37° C. are especially useful in the colloidal dispersions of the invention. In a similar manner, the following table can be used as guidance in selecting the liquid dispersed phase, depending on which organism is to be studied:

| ORGANISM | RECTAL TEMPERATURE (degrees Fahrenheit) |
| --- | --- |
| Swine (*Sus scrofa*) | 101.5–102.5 |
| Sheep (Ovis sp.) | 101–103 |
| Rabbit (*Oryctolaqus cuniculus*) | 102–103.5 |
| Rat (*Tattus morvegicus*) | 99.5–100.6 |
| Monkey (*Macaca mulatta*) | 101–102 |
| Mouse (*Mus musculus*) | 98–101 |

13
-continued

| ORGANISM | RECTAL TEMPERATURE (degrees Fahrenheit) |
| --- | --- |
| Goat (*Capra hircus*)) | 101–103 |
| Guinea pig (*Cavia porcellus*) | 102–104 |
| Hamster (*Mesocricetus* sp.) | 101–103 |
| Man (*Homo sapiens*) | 98.6–100.4 |
| Horse (*Equus* sp.) | 101–102.5 |
| Dog (*Canin familiaris*) | 101–102 |
| Baboon (*Papio*) | 98–100 |
| Cat (*Felis catus*) | 101–102 |
| Cattle (*Bos taurus*) | 101.5–102.5 |
| Chimpanzee (*Pan*) | 96–100 |

EXAMPLE 3

A colloidal dispersion was formed by comminuting, using the method and criteria of Example 45 below, an organic halide.

Specifically, a 100 mL quantity of a formulation was created containing: poloxamer 488, 2.5% v/v; fluorine-containing surfactant Zonyl FSN 2.5% v/v; sodium perfluorooctanoate, pH 7.0, 0.1% w/v; sodium chloride, 0.9%, w/v; and dodecafluoropentane, 2.0%, v/v. After low shear mixing, these were comminuted in the Microfluidizer model 110Y at 4° C. for eight passes. The milky emulsion was aliquoted into serum vials and sealed.

Within 72 hours, the particle size and size distribution was determined at 19° C. using the Nicomp model 370 (Nicomp Particle Sizing, Santa Barbara, Calif.). The mean diameter of the Gaussian analysis of the emulsion was 90.1 nm (number weighted) with a standard deviation of 48%. The volume weighted mean diameter was 316 nm.

EXAMPLE 4

The particle size and size distribution were determined at various steps or under different conditions during the formulation of an emulsion.

A 20 mL quantity of an emulsion was formulated, containing sodium perfluorooctanoate, pH 7.2, 2.5%, w/v, and dodecafluoropentane, 2%, w/v. These ingredients were added to water and the suspension cooled to 4° C. The Emulsiflex-1,000 (Avestin, Inc., Ottawa, Canada) was used to "pre-mix" the solution before final comminution.

Following 20 passes of the solution between two 10 mL syringes, the white, milky suspension was placed in the Nicomp 370 to determine particle size. This pre-mix suspension had a mean particle size (number weighted) of 452 nm and (Volume weighted) of 2398 nm.

The final emulsion was then formed by comminution through eight passes with the Emulsiflex-1,000 (Avestin, Inc., Ottawa, Canada) operating manually at a pressure of up to 7 MPa. The emulsion particles were much smaller, with a number-weighted mean diameter of 201 nm and a volume weighted mean diameter of 434 nm.

Aseptic filling of the material was achieved by passing the material through a 0.45 micron sterile filter (Gelman Acrodisc, Ann Arbor, Mich.). The final, sterile colloidal dispersion had a number weighted mean diameter of 160 nm.

EXAMPLE 5

The mean particle size measurement of an emulsion immediately after comminution is a useful test of the ultimate stability of the formulation. The following emulsions illustrate this point: A 2%, v/v, dodecafluoropentane emulsion was formulated containing 2% Pluronic P-123 and 2.6% Zonyl FSO, according to the method of Example 19 below. The mean particle diameter was 151 nm, with a 35% standard deviation. This emulsion was stable for at least six weeks, as judged by physical appearance and particle size.

To the same formulation was added 0.25% sodium perfluorooctonate. Although it was speculated this might further stabilize the formulation because this addition reduces interfacial tension, the high anionic charge density this surfactant could generate at the emulsion interface may actually prevent production of small particles. In fact, the immediate particle size measurements indicated a mean particle size of 1060 nm with a standard deviation of 106%. This emulsion degraded in a matter of days.

EXAMPLE 6

The particle size distribution of an emulsion can be measured by centrifugation. A sample of the emulsion of Example 19 below was placed in the Horiba CAPA-700 Particle Analyzer (Horiba Instruments, Irvine, Calif.). The particle size distribution, based on assuming the particles have a density of 1.66 g/cu cm, was as follows:

| Particle Size Range microns | Volume Percent |
| --- | --- |
| 0.0–0.5 | 12 |
| 0.5–1.0 | 26 |
| 1.0–1.5 | 22 |
| 1.5–2.0 | 15 |
| 2.0–2.5 | 7 |
| 2.5–3.0 | 0 |

EXAMPLE 7

The long term stability of the emulsions of the present invention was determined. The emulsion described in Example 19 below was placed at 19° C. and the particle size determined at intervals using the Nicomp 370. The results are contained in the following table:

| Time (days) | Mean Particle Diameter nm |
| --- | --- |
| 5 | 194 |
| 13 | 216 |
| 19 | 245 |
| 27 | 258 |
| 33 | 289 |
| 41 | 283 |
| 47 | 306 |
| 61 | 335 |
| 89 | 305 |

This emulsion initially grew rapidly from 194 to nm over the first month. However, since then the growth has largely stopped. Extrapolation of the curve of a graph of diameter vs time supports at least a one year stability for this emulsion.

EXAMPLE 8

The emulsion of Example 42 below was used to test the imaging capabilities of these colloidal dispersions administered by various routes. An approximately 20 kg mongrel dog was anesthetized with sodium barbiturate, and prepared for ultrasound examination according to the method described in Example 38.

A 0.2 mL/kg intravenous injection produced a strong contrast signal in the right and left Ventricles of the heart within the first minute following the injection. Doses of 0.5 mL/kg produced a strong Doppler signal in all organs examined, including the vascular system, liver, kidneys, heart, and vessels of the central nervous system.

A 0.5 mL injection either by an intradermal, intracutaneous, or intramuscular route caused local contrast, permitting examination of the musculoskeletal system.

A 1000 mL solution, prepared by diluting 50 mL of the emulsion of Example 42 into 950 mL of saline, was given by the oral route, effectively providing an intragastric and intraduodenal intraluminal administration. The lumen of the gastrointestional system was enhanced, providing better visualization of the liver, spleen, and internal reproductive organs.

A 10 mL volume of the emulsion of Example 42 below was administered by the intracystic route, affording enhanced visualization of the urinary bladder.

The above specific examples could be used to provide useful ultrasound contrast with the colloidal dispersions of the present invention by additional routes of administration. Specifically, the emulsions could be given by any of the following routes, among others: intraabdominal, intraarterial, intraarticular, intracapsular, intracervical, intracranial, intraductal, intradural, intralesional, intralocular, intralumbar, intramural, intraocular, intraoperative, intraparietal, intraperitoneal, intrapleural, intrapulmonary, intraspinal, intrathoracic, intratracheal, intratympanic, intrauterine, and intraventricular. Methods for administration by these routes can be found in a standard radiology text, such as "Pharmaceuticals in Medical Imaging," edited by D. P. Swanson, H. M. Chilton, J. H. Thrall. MacMillian Publishing Co., Inc., 1990, which text is incorporated herein by reference.

In addition to the above indicated organs or organ systems studied, one could study the lungs, breast, prostate, and endocrine systems by known means. The kinds of medical conditions amenable to study with the agents of the present invention are numerous. They include metabolic, traumatic, congenital, neoplastic, or infectious diseases. A description of the use of ultrasound imaging in these conditions can be found in the text "Diagnostic Ultrasound," edited by C. M. Rumack, S. R. Wilson, J. W. Charboneau, Mosby Year Book, Boston, 1991, incorporated herein by reference.

EXAMPLE 9

The colloidal dispersions of the present invention can produce a contrast effect in the ultrasound signal at concentrations ranging from 0.00001% w/v to 166% w/v.

If a 1% emulsion (such as the emulsion of Example 42) is diluted ten-fold (by adding one mL to nine mL of buffer) and a 0.1 mL aliquot added to 1000 mL water at 37° C. and the ultrasound intensity measured, there is a substantial increase in the backscatter. Specifically, the signal intensity, measured with the system described in Example 1, increases from 2.7 to 9.8 within the first minute following the above addition. At a greater dilution, the backscatter is indistinguishable from background. Thus, the lower limit for the concentration of the dispersed phase material is 0.00001%.

If 5 mL of dodecafluoropentane is added to 5 mL of water containing the surfactant mixture described in Example 25 below, and the suspension comminuted for 5 minutes by the method of Example 4, a 166% w/v emulsion is formed. This can be immediately administered, for example orally, to an organism to afford excellent ultrasound contrast. This amount represents a high end to the concentration of the dispersed phase material because higher concentrations produce formulations which tend to be unstable.

EXAMPLE 10

Proteins can be used to stabilize the colloidal dispersions of the present invention. Using high-intensity ultrasound, one can synthesize aqueous suspensions of proteinaceous microspheres filled with nonaqueous liquids (i.e., microcapsules). These are distinct from the ultrasound contrast agents of U.S. Pat. Nos. 4,718,433 and 4,774,958, which contain only gases, and follow the methods described by Suslick and Grinstaff (Suslick K. S., Grinstaff M. W. :Protein microencapsulation of nonaqueous liquids. *J Amer Chem Soc* 112:7807–7809, 1990). This reference describes only the use of high boiling nonaqueous liquids (which are unsuitable as ultrasound contrast agents) and fails to disclose the use of either low boiling liquids in general, or organic halides, in particular, as the nonaqueous liquids.

Proteinaceous microspheres can be synthesized with a high intensity ultrasound probe (Heat Systems, W375, 20 kHz, 0.5 in. Ti horn) from human serum albumin or hemoglobin. Typically, 5% pentane or 3% diethyl ether and 5% albumin are irradiated for three minutes at an acoustic power of about 150 W/sq cm, at 23° C. and a pH of 7.0. The resulting dispersion has a Gaussian distribution and a mean particle diameter of about 2.3 microns. They maintain their particle size for up to two months at 4° C.

In addition to albumin or hemoglobin, the following proteins can be used: alpha-1-antitrypsin, alpha fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, myoglobin, immunoglobulins, lactate dehydrogenase, lipase, lipoproteins, acid phosphatase, alkaline phosphatase, alpha-1-serum protein fraction, alpha-2-serum protein fraction, beta protein fraction, gamma protein fraction, gamma-glutamyl transferase.

In addition to pentane or diethyl ether, other aliphatic hydrocarbons, organic halides, and ethers can be used as described above for pentane.

EXAMPLE 11

The relationship of the size of the particles of the colloidal dispersion as an emulsion or microemulsion and the size of the microbubbles formed upon phase shift can be determined.

An aliquot of the emulsion of Example 27 below was placed in the Nicomp 370, operating at 19° C. and the mean particle size of the liquid emulsion was determined to be 231.7 nm. The temperature control of the instrument was adjusted to 37° C. and after temperature equilibration, which took about five minutes, the particle size was redetermined. The microbubble dispersion formed had a mean particle size of 1701.5 nm, an increase in size of 7.34-fold.

One can also calculate the expected change in dispersion size if one knows the relative densities of the dispersed liquid as a gas and liquid. For example, the Gas Data Book, by W. Braker and A. Mossman, Matheson, contains such data. Examining octafluorocyclobutane, one finds that 1 L of the liquid yields 188 L of gas at a pressure of 760 mm Hg and 15° C. Since the volume of a sphere is related to the diameter of a sphere by the cubic root of the volume, the phase transition for an octafluorobutane emulsion particle will cause a 5.7-fold increase in diameter.

EXAMPLE 12

The safety of the emulsions of the present invention is dramatically demonstrated in the mini-pig. Albunex brand ultrasound contrast agent, under development and the subject of U.S. Pat. Nos. 4,718,433 and 4,774,958, shows grave hemodynamic effects in the pig (Ostensen J., Hede R., Myreng Y., Ege T., Holtz E.) Intravenous injection of Albunex microspheres causes thromboxane mediated pulmonary hypertension in pigs, but not in monkeys or rabbits. Acta Physiol Scand 144:307–315, 1992). At doses as low as 0.001–0.05 mL per kg hypotension results. One pig died after a slow infusion of 0.05 mL per kg.

An experiment was performed in a 30 kg mini-pig under halothane anesthesia, using the protocol of the above reference. The results are contained in the following table:

| Dose, mL/kg | Cumulative Dose, mL/kg | Hemodynamic Effect |
|---|---|---|
| 0.01 | 0.02 | None |
| 0.02 | 0.03 | None |
| 0.05 | 0.08 | None |
| 0.10 | 0.18 | None |
| 0.20 | 0.38 | None |
| 0.30 | 0.68 | None |
| 0.40 | 1.08 | None |
| 0.50 | 1.58 | None |
| 0.60 | 2.18 | None |
| 0.60 | 2.78 | None |
| 0.80 | 3.58 | None |
| 0.30 | 3.88 | None |
| 2.00 | 5.88 | labored breathing |

All doses provided good cardiac contrast. The doses above 0.4 mL/kg provided Doppler enhancement of the liver as well.

In conclusion, injections of an emulsion of the present invention at 40-times the lethal dose of albumin microspheres in the mini-pig had minimal, transient effects. The threshold dose for an effect with Albunex is 0.001 mL per kg of the albumin microspheres or 2000-times below the threshold dose for an effect of the colloidal dispersions of the present invention.

EXAMPLE 13

The selection of amphiphilic materials with the proper hydrophilic-lipophilic balance (HLB) number for the selected dispersed phase is important for the stability of the colloidal dispersion. One way to determine the HLB number is to measure the interfacial tension of various surfactant mixtures. (A good general review of the HLB method can be found in: Emulsions: Theory and Practise, Paul Becher, Robert E. Krieger Publishing Company, Malabar, Fla., 1965, pp.232–252, incorporated herein by reference).

Mixtures of Pluronic P-123 and Pluronic F-127 were formed, yielding a 1% solution, v/v, with graded HLB numbers and the interfacial tension (IFT) of the solutions against dodecafluoropentane determined at 4° C., using a Kruss Drop Volume Tensiometer DVT-10, Kruss USA, Charlotte, N.C. The results are contained in the following table:

RELATIONSHIP BETWEEN HLB AND INTERFACIAL TENSION

| P-123 | F-127 | HLB | IFT (dynes/cm) |
|---|---|---|---|
| 1.00 | 0.00 | 8 | 27.07 |
| 0.86 | 0.14 | 10 | 23.94 |
| 0.75 | 0.25 | 12 | 23.58 |
| 0.60 | 0.40 | 14 | 22.48 |
| 0.50 | 0.50 | 15 | 22.80 |
| 0.40 | 0.60 | 16 | 23.16 |
| 0.25 | 0.75 | 19 | 23.61 |
| 0.00 | 1.00 | 22 | 26.36 |

The above data, when graphed, indicate an HLB for dodecafluoropentane of about 14. The use of amphiphilic materials, such as anionic, nonionic, cationic, or zwitterionic surfactants with an HLB number of 14 will provide the greatest stability for emulsions of the above liquid dispersed phase.

EXAMPLE 14

The interfacial tension between the liquid dispersed phase and the liquid continuous phase can be used to develop formulations, since this property has a significant influence on the stability of the colloidal dispersion.

The Ostwald ripening theory predicts a strong dependence of particle size stability on interfacial tension (reviewed by Kabalnov A. S., Shchukin E. D.; Ostwald ripening theory: Applications to fluorocarbon emulsion stability, Advances in Colloid and Interface Science, 38:69–97, 1992, incorporated herein by reference). The theory predicts stability and interfacial tension are inversely proportionate to each other. For example, if one can add amphiphilic materials which provide a five-fold lowering of interfacial tension, one will obtain a five-fold increase in stability.

Interfacial tensions of various amphiphilic materials in aqueous solutions (all expressed as v/v solutions) against dodecafluoropentane were measured at 4° C. and emulsions created from each formulation, as described in Example 13.

Pluronic P-123, 1%, and dodecafluoropentane had an interfacial tension of 27.1 dynes/cm and did not form a stable emulsion.

Pluronic F-127, 1%, and dodecafluoropentane had an interfacial tension of 26.4 dynes/cm and did not form a stable emulsion.

Zonyl FSO, 1%, and dodecafluoropentane had an interfacial tension of 5.8 dynes/cm and formed a stable emulsion.

Pluronic P-123, 0.33%, Pluronic F-127, 0.33%, and Zonyl FSN, 0.33%, and dodecafluoropentane had an interfacial tension of 14.1 dynes/cm and did form a stable emulsion.

Pluronic P-123, 1%, Zonyl FSO, 1.0%, sodium chloride, 1%, and sodium perfluorooctanoate, 0.5%, and dodecafluoropentane had an interfacial tension of 2.71 dynes/cm and formed a stable emulsion.

Thus, amphiphilic materials with interfacial tensions below 26 dynes/cm were required to form stable emulsions. Related findings would be obtained with other organic halides or with aliphatic hydrocarbons or ethers.

EXAMPLE 15

The viscosity of the liquid continuous phase can be used to develop formulations, since this property has a significant influence on the stability of the colloidal dispersion.

The Ostwald ripening theory predicts a strong dependence on particle size stability and viscosity (see Kabalnov A. S., et al. in Example 14). The theory predicts stability and viscosity are directly proportionate to each other. For example, if one can add viscogens (viscosity enhancing agents) which provide a five-fold increase in viscosity, one will, in general, obtain a five-fold increase in stability.

Examples of viscogens include, but are not limited to, carboxymethylcellulose, sorbitol, iohexol, other iodinated x-ray contrast materials, dextrose, polyethylene glycols. The emulsion of Example 38 below was prepared with or without 5% polyethylene glycol (PEG) 200, which produced a viscosity of 1.1 cP, and stability noted. The emulsion containing 5% PEG 200 had greater stability.

EXAMPLE 16

The ultrasound backscatter from dispersions of the emulsions of Examples 44 and 18 below were measured with a Hewlett Packard Model 77020 ultrasound scanner to determine the relative potency of the phase shift colloids of the present invention, which are liquid-liquid emulsion dispersions at room temperature but which become microbubbles following administration with either stable emulsions, as described by Long and others (U.S. Pat. Nos. 7,767,610, 4,987,154, and JP 2196730), Davis and others (EP 245019), and JP Patent 1609986 and JP 63060943), or with true air microbubbles, as described in EP 467031, EP 458745, WO 9115244, U.S. Pat. Nos. 5,088,499, 5,123,414, U.S. Pat. No. 4,844,882, U.S. Pat. No. 4,832,941, U.S. Pat. No. 4,466,442, and U.S. Pat. No. 4,276,885, each of which is incorporated herein by reference.

The air microbubbles were created by the following procedure. Introduce 0.5 mL of air into a 10 mL syringe and 10 mL of a 1.0%, v/v, solution of Pluronic F-68 into another 10 mL syringe, which is connected to the first syringe by a three-way stopcock. Pass the liquid and air back and forth between the two syringes rapidly. After about five passes the air and liquid have mixed and the solution has a milky, white appearance. Continue mixing for a total of 20 passes. A 1.0 mL sample of the gas dispersion added to 250 mL of water gave an ultrasound image with an intensity similar to hepatic tissue (4+strength). Surprisingly, the intensity of the ultrasound backscatter produced by the air microbubbles decreased rapidly, so that within five minutes the backscatter had returned to base line. This lack of persistence limits the diagnostic utility of air microbubbles.

On the other hand, 1.0 to 10.0 mL of a perfluorohexane emulsion in 250 mL of water at 37° C. yielded an ultrasound image similar to flowing blood (0-1+strength), indicating that these formulations produce ultrasound contrast only at extremely high dosages, which limit their general utility.

A 1.0 mL sample of the dodecafluoropentane emulsion diluted in 250 mL of 37° C. water yielded an ultrasound image with the intensity of the microbubble solutions (4+strength).

Parenthetically, all three experimental solutions were visually cloudy solutions of nearly equal apparent turbidity.

These experiments demonstrate that the ultrasound contrast agents of the present invention show greater persistence and/or potency then the prior art ultrasound contrast agents to a diagnostically useful extent.

EXAMPLE 17

A 1.0 mL sample of the contrast agent of Example 19 was withdrawn from a vial with a 1.0 mL syringe equipped with a 21-gauge needle and approximately 0.2 mL placed on a glass slide. A glass cover slip was placed over the liquid and the sample placed on the stage of a light microscope equipped with an eye piece micrometer, a temperature-controlled chamber, a 35-mm camera, and a Panasonic video camera.

The emulsion was examined under oil-immersion at 20° C. At this temperature the emulsion consisted of 0.2-0.3 micron particles which were undergoing rapid Brownian motion.

The temperature control was changed to 37° C. and the emulsion observed and images recorded. As the temperature rose the particles would individually suddenly grow in size until at 37° C. the emulsion had become a collection of 1-3 micron bubbles. The bubbles, in distinction to the liquid emulsion, were easily deformable. They did not, however, appear to coalesce. After 40 minutes of experimentation the microbubble ensemble remained intact and stable.

EXAMPLE 18

The criticality that some portion of the liquid dispersed phase undergo a liquid to gas phase transition at the body temperature of the organism to be imaged, in this case using an example temperature of 37° C., to the utility as an ultrasound contrast agent was tested by subjecting a series of emulsions, each with different liquid dispersed phases, to ultrasound imaging at 37° C.

The following emulsions were formulated or obtained from sources and 1.0 mL aliquots placed in 1000 mL of water at 37° C. The emulsion formed with 1-iodoperfluorooctane was formulated according to the methods disclosed by Long and others (U.S. Pat. Nos. 4,767,610, 4,987,154 and JP 2196730). The emulsion with perfluorodecalin was formulated according to the disclosures of JP Patent 1609986 and JP 63060943. The emulsion with triolean was formulated according to methods disclosed by Davis and others (EP 245019). The contents of each of these patents are hereby incorporated by reference. Ultrasound images were obtained of the solution before and after the addition and the results expressed as a percentage of enhancement times the length of time over which enhancement was observed.

| Dispersed Phase | Amphiphilic Material/Class D.P. | Boiling Point (°C.) | Enhancement Percent-Minutes X1000 |
|---|---|---|---|
| Decaflurobutane | Octadecylamine HCl/Cationic | −5.8 | 625 |
| Dodecafluropentane | Poloxamer-Zonyl/Nonionic | 29 | 740 |
| Perfluorohexane | Dodecylsulfate/Anionic | 59 | 178 |
| Perfluorooctane | Poloxamer-Zonyl/Nonionic | 98 | 24 |
| Perfluorodecalin | Poloxamer-Phospholipid-Oleate/Mixed | 141 | 8 |
| 1-Iodoperfluorooctane | Phospholipid/Zwitterionic | 160 | 6 |

-continued

| Dispersed Phase | Amphiphilic Material/Class D.P. | Boiling Point (°C.) | Enhancement Percent-Minutes X1000 |
|---|---|---|---|
| Triolean | Phospholipid/Zwitterionic | 235 | 0.2 |
| Saline | Not Applicable | Shaken | 0.006 |

As indicated above, the preferred formulations are the emulsions which undergo a complete phase shift at or below 37° C. However, the high vapor pressure liquids perfluorohexane and perfluorooctane which have vapor pressures at ambient temperature above 20 Torr, provided useful contrast and show improved contrast when compared to agitated saline or perfluorodecalin which has a vapor pressure at ambient temperature below 20 Torr.

EXAMPLE 19

The ultrasound contrast agents of the present invention can be made with the following equipment and steps: Microfluidizer, Model 110Y, Interaction chamber pressure 14,000 PSI; Pressure vessels, 316 steel, 5 L and 12 L sizes; Filters, cellulose acetate, 0.22 micron; Filter holders, 142 mm. The following solutions were made: 25% (w/v) sorbitol, 12 L; 2.5% w/v sodium perfluorooctanoate (PCR, Inc., Gainsville, Fla.); 60 g Pluronic P-123, 60 g Zonyl FSO, 7 mL 2.5% sodium perfluoro-octanoate solution, 1 L, sonicate to aid dissolution (stock surfactant solution). The Microfluidizer was primed with the sorbitol solution. The interaction chamber, tubing, and cooling coil are covered with chipped ice during the comminution process. To a 5 L pressure vessel with stir bar in an ice bath add sequentially: 500 mL sorbitol solution; 500 mL stock surfactant solution; 800 mL water; 200 g dodecafluoropentane. Pressurize vessel to 10 PSI with nitrogen for 45 min. Pass the suspension through the Microfluidizer for 45 min at 14,000 PSI. Transfer the emulsion to a vessel containing 8 L of 25% sorbitol at 4° C. and mix well. Transfer the emulsion to 100 mL vials using positive pressure, passing the material through a 0.22 micron filter in the process. Cap and seal the vials. The amphiphilic materials of this Example, including fluorine-containing surfactants and polyoxypropylene-polyoxyethylene glycol nonionic block co-polymers, produce a formulation with acceptable stability.

EXAMPLE 20

A 0.4 ml portion of n-pentane (Aldrich Chemical, Milwaukee, Wis.) was added to 2.0 mL of water at 4° C. Two clear separated phases resulted. NaCl was added (0.4 mL of a 10% w/v solution) to make a total of 2.8 mL. Approximately 135 mg of phosphatidyl lecithin (Sigma Chemical, St. Louis, Mo.) was added with stirring and the resulting slurry mixed by vigorous vortex agitation. The milky white solution separated into two phases within 5 min. upon standing. Ethanol was added in 0.1 mL increments with mixing to a total of 1.74 mL. There was no change in the appearance of the two-phase mixture. The formulation of this Example showed good in vitro ultrasound backscatter characteristics and demonstrates the use of aliphatic hydrocarbons having six or fewer carbon atoms and 17 total atoms.

EXAMPLE 21

A milky suspension was formed by adding together 1.80 mL water, 0.2 mL 10% NaCl, 0.1 mL ethanol, and 100 mg lecithin. A 0.1 mL portion of dodecafluoropentane (PCR, Gainsville, Fla.) was added and following mixing two phases were obtained. A 0.1 mL portion of n-pentane was added and then 0.2 mL dodecafluoropentane aliquots were added to bring the total dodecafluoropentane to 20% v/v. The resulting suspension was mixed and three phases obtained, two milky phases and a small clear phase. Additional NaCl was added to bring the solution to 7% and a 1 mL aliquot of ethanol added with no change in the character of suspension. The formulation of this Example showed good in vitro ultrasound backscatter characteristics and demonstrates the use of mixtures of a hydrocarbon and a fluorocarbon.

EXAMPLE 22

To a 2.0 ml portion of dodecafluoropentane was added 330 mg of lecithin. Following mixing, 1.0 mL of water was added and the suspension further mixed. A milky colloidal dispersion was formed. A milky colloidal dispersion was formed, demonstrating the use of a single surfactant as the amphiphilic material, in this case a naturally-occurring zwitterionic surfactant. Useful contrast agents are formed by replacing the portion of dodecafluoropentane in the formulation with an ether, such as, methyl ether, diethyl ether, or vinyl ether.

EXAMPLE 23

A 0.46 g portion of sodium dodecylsulfate (SDS) was added to 0.72 mL water and 8.00 mL dodecane. A 1.47 mL aliquot of pentanol was slowly added. Initially the suspension contained white, "filamentous" SDS in a clear fluid. A 1.0 mL addition of pentanol and gentle mixing lead to a substantial dissolution of the SDS. A 0.5 mL addition of pentanol with mixing lead over 10–15 min at room temperature to a clear, monophasic microemulsion. This formulation produced rather poor acoustic backscatter, demonstrating that a colloidal dispersion containing a liquid dispersed phase with an ambient temperature vapor pressure of less than 20 mm Hg, here exemplified by dodecane, is unsuitable as an ultrasound contrast agent.

EXAMPLE 24

The composition of the water, pentanol, dodecane, sodium dodecylsulfate microemulsion of Example 23 was varied to determine the compositional boundaries of the microemulsion. The following mixtures were prepared at room temperature and the appearance following 30 min. of stirring was noted:

| | Volume of Addition (mL) | | | | |
|---|---|---|---|---|---|
| EXPERIMENT | WATER | PENTANOL | DODECANE | SDS | APPEARANCE |
| 5-1 | 1.00 | 1.00 | 1.00 | 372 mg | Clear |
| 5-2 | 1.10 | 1.00 | 1.00 | 372 mg | Clear |
| 5-3 | 1.20 | 1.00 | 1.00 | 372 mg | Clear |
| 5-4 | 1.30 | 1.00 | 1.00 | 372 mg | Clear |
| 5-5 | 1.50 | 1.00 | 1.00 | 372 mg | Milky |
| 5-6 | 1.50 | 1.10 | 1.00 | 372 mg | Milky |
| 5-7 | 1.50 | 1.30 | 1.00 | 372 mg | Milky |
| 5-8 | 1.50 | 1.50 | 1.00 | 372 mg | Slt. Milky |
| 5-9 | 1.50 | 1.60 | 1.00 | 372 mg | Clear, Bluish Cast |

The 5–9 microemulsion became milky upon heating (greater than about 45° C.) and became clear, with a bluish cast, again upon cooling to room temperature. This reversible change in appearance could be repeated through at least six temperature shift cycles.

EXAMPLE 25

A 0.51 mL portion of octyl amine (Sigma Chemical Corp., St. Louis, Mo.) was added to 1.0 mL of water to form a clear solution. A 1.0 mL portion of octane was added and the clear solution became milky. A 0.49 mL portion of octanoic acid was added and the solution became a gel. A 0.17 mL aliquot of a 3.6M KOH solution dissolved the gel to produce a clear microemulsion. Five additions of water in 0.1 mL aliquots with mixing continued to yield a clear microemulsion. The sixth addition converted the clear emulsion to a milky colloidal dispersion. This Example demonstrates the formulation of an aliphatic hydrocarbon-containing emulsion with amphiphilic material comprising cationic surfactants.

EXAMPLE 26

A 1.0 mL portion of dodecafluoroheptanol (PCR) was added to 1.0 mL of dodecafluoropentane to form a clear, homogenous solution. The same quantity of octafluoropentanol in dodecafluoropentane yielded two clear, non-mixing phases. The addition of 2.0 to 4.0 mL water to the dodecafluoroheptanol-dodecafluoropentane yielded two non-mixing phases. Upon cooling to 4° C. the two clear phases changed to three clear phases.

EXAMPLE 27

A solution of 10% (v/v) Fluorad FC-430 (3M Chemical, St. Paul, Minn.) in water was prepared by adding 10 mL FC-430 to 100 mL water at room temperature and mixing. To 5 mL of this solution 1.0 mL dodecafluoropentane and 1.0 mL octafluoropentanol was added to yield an emulsion.

EXAMPLE 28

A 2.0 ml portion of 10% v/v FC-430 solution was added to 2.0 mL dodecafluropentane and two phases resulted. The addition of 0.3 mL dodecafluoroheptanol yielded a milky, white emulsion.

EXAMPLE 29

A 1 mL portion of 1.26M 2-amino-2-methyl-1-propanol (AMP) perfluorooctanoate was added to 1.0 mL of dodecafluoropentane, and 1 mL of 25% Pluronic F68 to yield two phases of milky liquid. A 0.05 mL addition of dodecafluoroheptanol yielded a single phase colloidal dispersion.

EXAMPLE 30

A 2.0 mL portion of a 15% (v/v) Pluronic F68 solution was added sequentially to 2.0 mL dodecafluoropentane and 0.2 mL dodecafluoroheptanol on ice. The mixture was taken up in a 5 mL glass syringe connected to a three-way stopcock and a second 5 mL glass syringe and forcefully passed back and forth between the syringes to yield a thick white emulsion.

EXAMPLE 31

The following mixture was formed by sequential addition at 4° C.: 2.0 mL 15% Pluronic F68, 2.0 mL dodecafluoropentane, 2.0 mL 0.2M AMP perfluoroctanoate, 0.1 mL dodecafluoroheptanol. The mixture was taken up in a 5 mL glass syringe connected to a three-way stopcock and a second 5 mL glass syringe and forcefully passed back and forth between the syringes to yield a thick white emulsion.

EXAMPLE 32

The following mixture was formed by sequential addition at 4° C.: 2.0 ml 15% Pluronic F68, 0.42 g D-sorbitol (Sigma) dissolved in 0.5 mL $H_2O$, 0.2 mL dodecafluoroheptanol, and 2.0 mL dodecafluoropentane. The mixture was taken up in a 5 mL glass syringe connected to a three-way stopcock and a second 5 mL glass syringe and forcefully passed back and forth between the syringes to yield a thick white emulsion.

EXAMPLE 33

The following mixture was formed by sequential addition at 4° C.: 2.0 mL of 15% (v/v) Pluronic F-68, 0.40 mL 0.1M Tris(hydroxymethyl) amino methane (Tris) perfluorooctanoate, pH 7.2, 2.0 mL dodecafluoropentane. The mixture was taken up in a 5 mL glass syringe connected to a three-way stopcock and a second 5 mL glass syringe and forcefully passed back and forth between the syringes to yield a white colloidal dispersion.

EXAMPLE 34

The following mixture was formed by sequential addition at 4° C.: 60 mL 25% Pluronic F68, 24 mL 1,1,7-H-dodecafluoroheptanol, 75.8 g dodecafluoropentane. The mixture was comminuted by batchwise mixing using 30 cc syringes, a three-way stopcock and 40 manual passages. The mixture was sequentially diluted 1:10 twice with a solution composed of 8.0 mL 25% Pluronic F68, 2.0 mL 50% D-sorbitol, 1.0 mL pH 7.2, 0.1M Tris perfluorooctanoate and further comminuted by syringe passage. This formulation was administered to mice, weighing 20–30 g, intravenously by tail vein injection and observed for seven days. The results are contained in the following table:

| DOSAGE (mL/kg) | OBSERVATIONS |
| --- | --- |
| 20 | Survival |
| 25 | Morbid but survival |
| 30 | Morbid but survival |
| 40 | No Survival |

This biocompatible colloidal dispersion was stable for at least two weeks after formulation.

EXAMPLE 35

The following formulation was prepared: 1.0 mL 25% polyethylene glycol 3550, 1.0 mL 50% sorbitol, 3.0 mL 15% (w/v) Pluronic F-68, 3.0 mL 20% (w/v) Fluorosurfactant FC 430, 0.4 mL 0.1M Tris perfluorooctanoate and 1.0% (v/v) dodecafluoropentane. The mixture was comminuted in a water bath sonicator by the application of acoustic energy at 4° C. for 10 min to yield a milky colloidal dispersion.

EXAMPLE 36

A series of solutions of aqueous media, each containing different proportions of amphiphilic materials, were formed and tested as the basis for a formulation.

Solution A: A clear solution containing 6.0 mL of a 25% solution of Pluronic F-68, 6.0 mL of a 50% solution of PEG3350, 0.60 mL 0.1M Tris perfluorooctanoate, and 2.4 mL $H_2O$.

Solution B: A clear solution containing 1.18 mL of a 25% solution of Pluronic F68, 6.0 mL of a 50% solution of PEG 3350, 0.12 mL Tris perfluorooctanoate and 7.7 mL $H_2O$.

Solution C: A turbid solution, containing a gelled precipitate, was obtained by mixing 6.0 mL of 50% PEG 3350, 0.75 mL Tris perfluorooctanoate and 1.5 mL $H_2O$. This solution is not biocompatible for intravascular administration but is biocompatible for oral, intraperitoneal, rectal or intrauterine administration.

Solution D: A clear solution was obtained by mixing 6.0 mL 25% (w/v) Pluronic F-68, 6.0 mL 50% (w/v) PEG 3350, 0.6 mL 0.1M Tris perfluorooctanoate and 2.4 mL $H_2O$.

Solution E: A clear solution was obtained by mixing 6.0 mL 50% (w/v) PEG 3350, 7.5 mL 20% (w/v) FC-430, 0.75 mL Tris perfluoroctanoate and 0.75 mL $H_2O$.

Solution F: A clear solution was obtained by mixing 1.8 mL 25% (w/v) Pluronic F-68, 6.0 mL 50% (w/v) PEG 3350, 0.12 mL 0.1M Tris perfluorooctanoate, and 7.7 mL $H_2O$.

Solution G: A clear solution, containing a tiny precipitate was formed by mixing a 3.0 mL Pluronic F-68 3.75 mL (w/v) FC-430, 6.0 mL PEG 3350, 0.68 mL Tris perfluorooctanoate, and 1.57 mL $H_2O$.

To 7.0 mL of solutions A–G a 0.14 mL portion of dodecafluoropentane was added at 4° C. The colloidal dispersions were created by 40 passes between two syringes using a three-way stopcock.

Formulation D was administered to mice via tail vein injection and had a LD50 of 20 ml/kg. Formulations F and G were toxic at 10 ml/kg.

EXAMPLE 37

An emulsion was formulated by mixing 45 mL of 20%. PEG 3350, 237 mg Pluronic F68, 0.225 mL Fluorad FC-171, 2.25 mL 0.1M Tris perfluorooctanoate, and 10% (v/v) dodecafluoropentane. This was comminuted by mixing in a two-syringe, three-way stopcock apparatus.

This formulation was biocompatible in a test of hemolysis. Whole blood was collected from a rat by intracardiac puncture (2.0 mL) in a EDTA-containing evacuated collection tube. A 0.10 mL aliquot of blood was added to a 0.20 mL aliquot of the above formulation to simulate the peak blood level obtained following an intravenous dosage of 100 mL/kg. The blood was mixed with the formulation for two minutes and the sample centrifuged. The supernatant was clear, the pellet deep red, indicating no hemolysis even at this extremely large dosage.

This formulation was also biocompatible in a test of acute toxicity by causing only minor, labored breathing in mice after intravenuous administration at 20 mL/kg.

EXAMPLE 38

A formulation containing dodecafluoropentane and amphiphilic materials in an aqueous media was tested for biocompatibility and utility as an ultrasound contrast agent. A stock solution of 90 mL of 20% PEG 3350, 474 mg of Pluronic F-68, 0.45 mL Flurorad FC-171, and 4.5 mL 0.1M Tris perfluorooctanoate was mixed and yielded a clear solution. To 9.0 mL of above was added 0.18 mL of dodecafluoropentane. A colloidal dispersion was formed by comminution between two 5 mL syringes.

An echocardiology study was performed in a 32 kg dog according to the model described by Keller M. W., Feinstein S. B., Watson D. D.: Successful left ventricular opacification following peripheral venous injection of sonicated contrast: An experimental evaluation. Am Heart J 114: 570d (1987), incorporated herein by reference. Eleven administrations of the above formulation were given intravenously at doses of 0.05 to 0.75 mL/kg. The 0.05 mL/kg dose gave only slight contrast enhancement of the right and left ventricles immediately following injection. All doses between 0.10 and 0.75 mL/kg gave diagnostically useful enhancement of the ventricular chambers. The injections had a minimal effect on hemodynamic parameters.

A 10% dodecafluoropentane emulsion was formed in the above formulated aqueous media and the contrast enhancement produced compared to the 2% formulation. At doses of 0.20 and 0.25 mL/kg this formulation produced intense cardiac chamber opacification following intravenous administration with minimal hemodynamic changes.

EXAMPLE 39

An emulsion containing a high density, high viscosity biocompatible aqueous medium as the continuous phase was formulated. It contained 0.06 mL of 15% Pluronic F68, 0.06 mL Zonyl FSO-100, 0.12 mL of 5% Zonyl FSN-100, 0.146 mL of 0.1M Tris perflurooctanoate, pH 7.2, 4.47 mL of 76% w/v iohexol (Omnipaque 350, Sterling Winthrop, N.Y.), and 0.6 mL of dodecafluoropentane. A stable formulation was formed following comminution by 2-syringe mixing. Other high density iodinated x-ray contrast materials could be substituted for iohexol. Use of water alone as the continuous phase medium yielded contrast agents which settled rapidly following formulation in the bottle. This example demonstrates the utility of a high density, high viscosity biocompatible aqueous medium as the continuous phase.

EXAMPLE 40

A series of polyoxypropylene-polyoxyethylene glycol nonionic block copolymers were tested for their ability to act as amphiphilic materials in stabilizing the formulations of dodecafluoropentane liquid-liquid emulsions. The following solutions were formed:

A—1.9 mL of 25% Pluronic F-68 and 0.04 mL dodecafluoropentane

B—1.9 mL of Pluronic L-121 and 0.04 ml dodecafluoropentane

C—1.9 mL of Pluronic L-122 and 0.04 mL dodecafluoropentane

D—1.9 mL of Pluronic L-121 and 0.04 mL dodecafluoropentane

E—1.9 mL of Pluronic L-101 and 0.04 mL dodecafluoropentane

F—1.9 mL of Pluronic L-92 and 0.04 mL dodecafluoropentane

G—1.9 mL of Pluronic L-81 and 0.04 mL dodecafluoropentane

H—1.9 mL of Pluronic P-123 and 0.04 mL dodecafluoropentane

The above solutions were placed in sealed glass tubes and vortex mixed at 4° C. for 10 min. The size and number of the dispersed dodecafluoropentane phase particles was accessed visually. Solution H yielded the smallest particles.

EXAMPLE 41

The relative hydrophilic-lipophilic balance (HLB) is a method of optimizing a nonionic surfactant solution to achieve greatest stability. It is described in detail in *Emulsions: Theory and Practice*, Paul Becher, 1965, Robert E. Krieger Publishing Company Malabar, Fla., and references contained therein, and is incorporated here by reference. Solutions of Pluronic L61 (HLB 3.0) and F68 (HLB 29) were mixed to achieve intermediate HLB values by the following formula:

$$HLB = f_{L61} \{HLB \text{ of } L61\} + f_{f68} \{HLB \text{ of } F68\}$$

The actual solutions, the calculated HLB values, and the stability of the final formulation (a 2% v/v emulsion of dodecafluorohexane) are contained in the following table:

| PLURONIC L61 | PLURONIC F68 | RELATIVE HLB | STABILITY |
| --- | --- | --- | --- |
| 9.6 mL | 0.4 mL | 4 | 0 |
| 8.8 | 1.2 | 6 | +++ |
| 8.1 | 1.9 | 8 | +++ |
| 7.3 | 2.7 | 10 | + |
| 6/5 | 3.5 | 12 | 0 |
| 5.8 | 4.2 | 14 | 0 |
| 5.0 | 5.0 | 16 | 0 |
| 4.2 | 5.8 | 18 | 0 |

0 = no stability; + = some stability; +++ = greatest stability

The relative HLB for perfluorohexane established by this work is 6–8. The greatest stability of perfluorohexane emulsions will be achieved by using amphiliphic materials with relative HLB values of 6–8, regardless of their chemical structure.

EXAMPLE 42

A large scale formulation of ultrasound contrast agents of the present invention can involve the following equipment and steps: Microfluidizer, Model 110Y, Interaction chamber pressure 14,000 PSI; Pressure vessels, 316 steel, 5 L and 12 L sizes; Filters, cellulose acetate, 0.22 micron; Filter holders, 142 mm. The following solutions were made: 25% (w/v) sorbitol, 12 L; 60 g Pluronic P-123, 60 g Zonyl FSO, 1 L; sonicate to aid dissolution (stock surfactant solution). The Microfluidizer was primed with the sorbitol solution. The interaction chamber, tubing, and cooling coil are covered with chipped ice during the comminution process. To a 5 L pressure vessel with stir bar in an ice bath add sequentially: 500 mL sorbitol solution; 500 mL stock surfactant solution; 800 mL water; 200 g dodecafluoropentane. Pressurize vessel to 10 PSI with nitrogen for 45 min. Pass the suspension through the Microfluidizer for 45 min at 14,000 PSI. Transfer the emulsion to a vessel containing 8 L of 25% sorbitol at 4° C. and mix well. Transfer the emulsion to 100 mL vials using positive pressure, passing the material through a 0.22 micron filter in the process. Cap and seal the vials.

EXAMPLE 43

A formulation of the present invention involves the following equipment and steps: Microfluidizer, Model 110Y, Interaction chamber pressure 14,000 PSI; Pressure vessels, 316 steel, 5 L and 12 L sizes; Filters, cellulose acetate, 0.22 micron; Filter holders, 142 mm. The following solutions were made: 62.5% (w/v) sorbitol, 10 L; 41.75 g Pluronic P-123, 41.75 g Zonyl FSO, 2.5 L, sonicate to aid dissolution (stock surfactant solution). The Microfluidizer was primed with the sorbitol solution. The interaction chamber, tubing, and cooling coil are covered with chipped ice during the comminution process. To a 5 L pressure vessel with stir bar in an ice bath add sequentially: 1800 mL stock surfactant solution; 200 g dodecafluoropentane. Pressurize vessel to 10 PSI with nitrogen for 45 min while stirring. Pass the suspension through the Microfluidizer for 30 min at 5,000 PSI and for 60 min at 14,000 PSI. Transfer the emulsion to a vessel containing 8 L of 62.5% sorbitol at 4° C. and mix well. Transfer the emulsion to 100 mL vials using positive pressure, passing the material through a 0.22 micron filter in the process. Cap and seal the vials.

EXAMPLE 44

A formulation of the present invention involves the following equipment and steps: Microfluidizer, Model 110Y, Interaction chamber pressure 14,000 PSI; Pressure vessels, 316 steel, 5 L and 12 L sizes; Filters, cellulose acetate, 0.22 micron; Filter holders, 142 mm. The following solutions were made: 33.3% (w/v) sucrose, 20 L; 150.0 g Pluronic P-123, 150.0 g Zonyl FSO, 2.5 L, sonicate to aid dissolution (stock surfactant solution). The Microfluidizer was primed with the sucrose solution. The interaction chamber, tubing, and cooling coil are covered with chipped ice during the comminution process. To a 5 L pressure vessel with stir bar in an ice bath add sequentially: 1800 mL stock-surfactant solution; 333 g dodecafluoropentane. Pressurize vessel to 10 PSI with nitrogen for 60 min while stirring. Pass the suspension through the Microfluidizer at 14,000 PSI for 160 min and with a circulating water bath cooling the interaction chamber to −3.0° C. Transfer the emulsion to a vessel containing 18 L of 33.3%, w/v, sucrose at 4° C. and mix for 45 min. Transfer the emulsion to 20 mL prechilled vials using positive pressure, passing the material through a 0.22 micron filter in the process. Cap and seal the vials.

EXAMPLE 45

The dispersed phase of the present invention should be composed of a high vapor pressure chemical, such that, at the body temperature of the organism to which the formulation is to be administered and which will be examined following administration by ultrasound, a sufficient quantity of the chemical becomes a gaseous dispersion to provide a diagnostically useful alteration in the ultrasound data obtained during the examination. In a preferred embodiment, the dispersed phase can be composed of any chemical which has a boiling point under standard pressure conditions below the body temperature of the organism which is to be administered the formulation and which will be examined following administration by ultrasound. Example 2 contains a table of the body temperatures of a number of species which can be used to select the appropriate dispersed phase for the formulations disclosed herein.

Under certain conditions, for example, organisms with febrile conditions or studies done in medical facilities at high altitudes, where the air pressure is lower, chemicals which have boiling points up to 18° C. above the normal body temperature of the organism could have utility as the dispersed phase for such ultrasound contrast agents.

Having set the upper temperature limit for selecting the dispersed phase low boiling liquid, the lower limit is determined by the manufacturing method. If the available equipment contains only sealed vessels, and one cannot pressurize the reaction vessel during the formulation of the colloidal dispersion, only dispersed phases with boiling points at or above the freezing temperature of the continuous phase can be used. For example, a continuous phase containing ca 25% w/v iohexol has a freezing point near −6° C. Using such a continuous phase, any low boiling liquid which boils above −6° C. can thus be liquified by cooling alone.

However if one can pressurize the reaction vessel, for example with a nitrogen tank operating at 30 lb. per sq in. pressure, one can potentially liquify and thus disperse any low boiling liquid, even those boiling at temperatures below the freezing point of the continuous phase.

Example 44 describes a method of forming an emulsion with a dispersed phase liquid which boils above the freezing point of the continuous phase, while Example 48 below describes a method of forming an emulsion by the application of both pressure and refrigeration with a dispersed phase liquid which boils below the freezing point of the continuous phase liquid. Obviously, any chemical will be more efficiently dispersed by using some positive pressure, to lower the vaporization of these materials with the substantial vapor pressures that a low boiling point implies.

Having determined the appropriate boiling point of the dispersed phase liquid, the actual chemicals which are useful can be quickly determined by reference to standard texts, such as the CRC or a similar compendium. A listing of some, but not all, low boiling liquids arranged by boiling point follows:

Chemical List: Boiling Points in degrees Celcius

| Chemical Name | Molecular Weight | Boiling Point | Chemical Group |
|---|---|---|---|
| Neon | 20.18 | −246.0 | 11 |
| Nitrogen (N2) | 28.01 | −196.0 | 11 |
| Argon | 39.98 | −189.4 | 10 |
| Oxygen(O2) | 32 | −183.0 | 11 |
| Methane | 16.04 | −164.0 | 1 |
| Krypton | 83.8 | −153.0 | 11 |
| Nitric oxide | 30.01 | −151.6 | 11 |
| Methane, tetrafluoro | 88 | −129.0 | 3 |
| Xenon | 131.29 | −108.0 | 11 |
| Ethylene | 28.05 | −103.7 | 1 |
| Ethane | 30.07 | −88.6 | 1 |
| Nitrous oxide | 44.01 | −88.5 | 11 |
| Acetylene | 26.04 | −84.0 | 1 |
| Methane, nitroso-trifluoro | 99.01 | −84.0 | 3 |
| Methane, trifluoro | 70.02 | −84.0 | 3 |
| Carbonyl fluoride | 66.01 | −83.0 | 9 |
| Ethylene, 1,2-difluoro | 64 | −83.0 | 3 |
| Ethylene, 1,1-difluoro | 64.04 | −83.0 | 3 |
| Methane, trifluoro | 70.01 | −82.2 | 3 |
| Methane, chloro trifluoro | 104.46 | −81.4 | 3 |
| Ethane, hexafluoro | 138.01 | −79.0 | 3 |
| Ethane, perfluoro | 138.01 | −79.0 | 3 |
| Methane, fluoro | 34.03 | −79.0 | 3 |
| Carbon dioxide | 44.01 | −78.6 | 11 |
| Methane, fluoro | 34.03 | −78.4 | 3 |
| Butyl nitrite | 103.12 | −77.8 | 11 |
| Ethylene, tetrafluoro | 100.02 | −76.3 | 3 |
| Sulfur hexafluoride | 146.05 | −64.0 | 11 |
| Trifluoroacetonitrile | 95.02 | −64.0 | 10 |
| Methane, bromo-trifluoro | 148.91 | −57.9 | 3 |
| Methane, difluoro | 52.02 | −51.6 | 3 |
| Ethylene, trifluoro | 82.03 | −51.0 | 3 |
| Carbonyl sulfide | 60.08 | −50.0 | 11 |
| Propyne, 3,3,3-trifluoro | 94.04 | −48.3 | 3 |
| Ethane, Pentafluoro | 120 | −48.0 | 3 |
| Propene | 42.08 | −47.4 | 1 |
| Ethane, 1,1,1-trifluoro | 84.04 | −47.3 | 3 |
| Propane | 44.1 | −42.1 | 1 |
| Ethane, nitroso-pentafluoro | 149.02 | −42.0 | 3 |
| Methane, chloro-difluoro | 86.47 | −40.8 | 3 |
| Propyl, 1,1,1,2,3,3-hexafluoro-2,3-difluoro | 221 | −39.03 | 3 |
| Allene, tetrafluoro | 112.03 | −38.0 | 3 |
| Ethane, 1-chloro-1,1,2,2,2-pentafluoro | 154.47 | −38.0 | 3 |
| Ethane, chloro pentafluoro | 154.47 | −38.0 | 3 |
| Ethane, fluoro | 48.06 | −37.7 | 3 |
| Dimethylamine, perfluoro | 171.02 | −37.0 | 10 |

Chemical List: Boiling Points in degrees Celcius

| Chemical Name | Molecular Weight | Boiling Point | Chemical Group |
|---|---|---|---|
| Propane, perfluoro | 188.02 | −36.0 | 3 |
| Ethyl amine, perfluoro | 171.02 | −35.0 | 10 |
| Allene | 40.06 | −34.5 | 1 |
| Cyclopropane | 42.08 | −32.7 | 1 |
| Trifluoromethyl peroxide | 170.01 | −32.0 | 11 |
| Azomethane, hexafluoro | 166.03 | −31.6 | 11 |
| Methane, nitro-trifluoro | 115.01 | −31.1 | 3 |
| Acetylene-chloro | 60.48 | −30.0 | 3 |
| Methane, dichloro difluoro | 120.91 | −29.8 | 3 |
| Propylene, perfluoro | 150.02 | −29.4 | 3 |
| Acetone, hexafluoro | 166.02 | −28.0 | 3 |
| Ethane, 1,1,2,2-tetrafluoro | 102.03 | −27.0 | 3 |
| Ethane, 1,1,1,2-tetrafluoro | 102.03 | −26.5 | 3 |
| Ethylene, 1-chloro-1,2,2-trifluoro | 116.47 | −26.2 | 3 |
| Ethylene, chloro trifluoro | 116.47 | −26.2 | 3 |
| Methyl ether | 46.07 | −25.0 | 6 |
| Ethane, 1,1-difluoro | 66.05 | −24.7 | 3 |
| 2-Butyne, perfluoro | 162.03 | −24.6 | 3 |
| Ethylene, 1-chloro-1-fluoro | 80.5 | −24.0 | 3 |
| Propyne | 40.06 | −23.2 | 1 |
| Methane, iodo-trifluoro | 195.91 | −22.5 | 3 |
| Trifluoromethyl sulfide | 170.07 | −22.2 | 11 |
| Methane sulfonyl fluoride, trifluoro | 152.06 | −21.7 | 3 |
| Propene, 3,3,3-trifluoro | 96.05 | −21.0 | 3 |
| Propene, 1,1,1,3,3-Pentafluoro | 132.04 | −21.0 | 3 |
| Methane, (pentafluorothio)trifluoro | 196.06 | −20.0 | 3 |
| Ethane, 1,2,2,2-Tetrafluoro | 102.04 | −19.7 | 3 |
| Ethylene, 2-chloro-1, 1-difluoro | 98.5 | −17.7 | 3 |
| Propene, 2-H-heptafluoro | 170.03 | −15.0 | 3 |
| Propane, 1,2,2-trifluoro | 98.07 | −13.0 | 3 |
| Methane, bromo difluoro nitroso | 159.92 | −12.0 | 3 |
| Methyl nitrite | 61.04 | −12.0 | 11 |
| Propane, heptafluoro-1-nitroso | 199.03 | −12.0 | 3 |
| Ethane, 2-chloro-1,1,1,2-tetrafluoro | 136.48 | −12.0 | 3 |
| Isobutane | 58.12 | −11.6 | 1 |
| Ethane, 1-chloro-1,1,2,2-tetrafluoro | 136.48 | −10.0 | 3 |
| Propane, 2-fluoro | 62.09 | −10.0 | 3 |
| Methane, chloro fluoro | 68.48 | −9.1 | 3 |
| Isobutylene | 56.11 | −6.9 | 1 |
| Dimethyl amine, hexafluoro | 153.03 | −6.7 | 10 |
| 1-Butene | 56.11 | −6.3 | 1 |
| Nitrosyl chloride | 65.47 | −5.5 | 11 |
| 1,3-Butadiene | 54.09 | −4.4 | 1 |
| Cyclobutane, octafluoro | 200.03 | −4.0 | 3 |
| Propylene, 3-fluoro | 60.07 | −3.0 | 3 |
| Dimethyloxonium chloride | 82.53 | −2.0 | 3 |
| Propane, 2-chloroheptafluoro | 204.47 | −2.0 | 3 |
| Propane, 1,1,1,2,2,3-Hexafluoro | 152.04 | −1.4 | 3 |
| Propane, 1,1,1,3,3,3-Hexafluoro | 152.05 | −1.1 | 3 |
| Methanesulfenylchloride, trifluoro | 136.52 | −0.7 | 3 |
| n-Butane | 58.12 | −0.5 | 1 |
| Propane, 2,2-difluoro | 80.08 | −0.4 | 3 |
| Ethane, 2-chloro, 1,1-difluoro | 100 | −0.1 | 3 |
| Ethane, nitro-pentafluoro | 165.02 | 0.0 | 3 |
| 2-Butene, perfluoro | 200.03 | 0.0 | 3 |
| Acetylene, isopropyl | 68 | 0.0 | 1 |
| 2-Butene {trans} | 56.11 | 0.9 | 1 |
| 1,2-Benzanthracene, 4-methyl | 242.32 | 1.0 | 2 |
| Propane, 1,1,1,2,2,3-hexafluoro | 152.04 | 1.2 | 3 |
| 2-Butene, octafluoro | 200.04 | 1.2 | 3 |
| Azomethane | 58.08 | 1.5 | 11 |
| Phthalic acid, tetrachloro | 303.91 | 2.0 | 3 |
| Trimethyl amine | 59.11 | 2.9 | 10 |
| Cyclobutene, perfluoro | 162.03 | 3.0 | 3 |
| 1-Butene, 3,3,4,4,4-Pentafluoro | 146 | 3.0 | 3 |
| Ethane, 1,2-dichloro-1,1,2,2-tetrafluoro | 170.92 | 3.0 | 3 |
| Ethane, 1,1-dichloro-1,2,2,2-tetrafluoro | 170.92 | 3.6 | 3 |
| 2-Butene (cis) | 56.11 | 3.7 | 1 |
| Ethane, 1,2-chlorotetrafluoro | 170.92 | 3.8 | 3 |
| Butane, decafluoro | 238.03 | 4.0 | 3 |
| Cyclopropane, methyl | 56.11 | 4.0 | 1 |
| Ethane, dichlorotrifluoro | 152 | 4.0 | 3 |
| Acetylene-bromo | 104.93 | 4.7 | 3 |
| 1-Butene, perfluoro | 200.03 | 4.8 | 3 |
| Benzoyl chloride, pentachloro | 312.79 | 5.0 | 3 |
| Ethane, 1,1,2-trifluoro | 84.04 | 5.0 | 3 |

-continued

| Chemical List: Boiling Points in degrees Celcius | | | |
|---|---|---|---|
| Chemical Name | Molecular Weight | Boiling Point | Chemical Group |
| Vinyl acetylene | 52.08 | 5.1 | 1 |
| 1,3-Butadiene, hexafluoro | 162.03 | 6.0 | 3 |
| Propene, 2-trifluoromethyl | 110.08 | 6.0 | 3 |
| Methanethiol | 48.1 | 6.2 | 11 |
| Propane, 1,1,1,2,3,3-Hexafluoro | 152.04 | 6.5 | 3 |
| Carbon suboxide | 68.03 | 6.8 | 11 |
| Ethane, 2-chloro-1,1,1-trifluoro | 118.49 | 6.9 | 3 |
| Fulvene | 78.11 | 7.0 | 11 |
| Dimethyl amine | 45.08 | 7.4 | 10 |
| Propane, 2-chloro-1,3-difluoro | 114.51 | 8.0 | 3 |
| 1-Butyne | 54.09 | 8.1 | 1 |
| Methane, dichlorofluoro | 102.92 | 9.0 | 3 |
| Neopentane | 72.15 | 9.5 | 1 |
| Ethylene, 1-chloro-2-fluoro | 80.5 | 10.0 | 3 |
| Butadiyne | 50.06 | 10.3 | 1 |
| 1,2-Butadiene | 54.09 | 10.8 | 1 |
| Ethyl methyl ether | 60.1 | 10.8 | 6 |
| 1,3-Butadiene, 2-fluoro | 72.08 | 12.0 | 3 |
| Crotononitrile | 67.09 | 12.0 | 11 |
| Cyclobutane | 56.11 | 12.0 | 1 |
| Isobutane, 1,2-epoxy-3-chloro | 106.55 | 12.0 | 3 |
| Methyl vinyl ether | 58.08 | 12.0 | 6 |
| Propane, 1-bromo-heptafluoro | 248.9 | 12.0 | 3 |
| Ethane, idopentafluoro | 245.9 | 12.0 | 3 |
| Propane, 2-(trifluoromethyl)-1,1,1,3,3,3-hexafluoro | | 211 | 12.03 |
| Ethane, Chloro | 64.51 | 12.3 | 3 |
| Diazoethane, 1,1,1-trifluoro | 110.04 | 13.0 | 3 |
| 2-Butene, 3-methyl | 68 | 14.0 | 1 |
| Methane, disilano | 76.25 | 14.7 | 11 |
| Ethyl nitrite | 75.07 | 16.0 | 11 |
| Ethyl amine | 45.08 | 16.6 | 10 |
| Tungsten hexafluoride | 298 | 17.5 | 11 |
| 2,3-Dimethyl-2-norbornano | 140.23 | 19.0 | 11 |
| Ethylene, 1,1-chloro-2,2-difluoro | 133 | 19.0 | 3 |
| Methane, bromo fluoro | 112.93 | 19.0 | 3 |
| 1-Butene, 3-methyl | 70.13 | 20.0 | 1 |
| Borine, trimethyl | 55.91 | 20.0 | 11 |
| Fluorinert, FC-87 (3M Trade Mark) | Unknown | 20.0 | 3 |
| Cyclopropane, 1,1-dimethyl | 70.13 | 20.6 | 1 |
| Acetaldehyde | 44.05 | 20.8 | 7 |
| Acetyl flouride | 62.04 | 20.8 | 9 |
| Borine, dimethyl, methoxy | 71.19 | 21.0 | 11 |
| Ethylene, 1,2-dichloro-1,2-difluoro | 132.92 | 21.1 | 3 |
| Ethylene, dichloro difluoro | 132.92 | 21.1 | 3 |
| Methane, difluoro-iodo | 177.92 | 21.6 | 3 |
| Diacetylene | 50.08 | 22.0 | 1 |
| Propylene, 2-chloro | 76.53 | 22.6 | 3 |
| Carvone- {d} | 150.22 | 23.0 | 11 |
| Methane, trichlorofluoro | 137.37 | 23.7 | 3 |
| 1,3-Dioxolane-2-one, 4-methyl | 102.09 | 24.2 | 1 |
| Methane, dibromo difluoro | 209.82 | 24.5 | 3 |
| 2-Pentanone, 4-amino-4-methyl | 115.18 | 25.0 | 10 |
| Methane, chloro difluoro nitro | 131.47 | 25.0 | 3 |
| Propane, heptafluoro-1-nitro | 215.03 | 25.0 | 3 |
| Cyclopentene, 3-chloro | 102.56 | 25.0 | 3 |
| 1,4-Pentadiene | 68.12 | 26.0 | 1 |
| 1,5-Heptadiyne | 92.14 | 26.0 | 1 |
| 3-Butene-2-one, 4-phenyl {trans} | 146.19 | 26.0 | 2 |
| Propane, 1,1,2,2,3-Pentafluoro | 134.06 | 26.0 | 3 |
| 2-Butyne | 54.09 | 27.0 | 1 |
| Ethane, 2,2-dichloro-1,1,1-trifluoro | 152.9 | 27.0 | 3 |
| Cyclopentene, Octafluoro | 211.05 | 27.0 | 3 |
| 1-Nonene-3-yne | 122.21 | 27.0 | 1 |
| 2-Methyl butane | 72.15 | 27.8 | 1 |
| Butane, 2-methyl | 72.15 | 27.8 | 1 |
| Ethane, 1,2-dichlorotrifluoro | 152.9 | 28.0 | 3 |
| Ether, difluoromethyl 2,2,2-trifluoroethyl | 150.05 | 28.0 | 3 |
| Cyclopropane, 1,2-dimethyl {trans, 1} | 70.13 | 28.0 | 1 |
| Vinyl ether | 70 | 28.0 | 6 |
| Cyclopropane, 1,2-dimethyl {trans, dl} | 70.13 | 29.0 | 1 |
| Toluene, 2,4-diamino | 122.17 | 29.0 | 2 |
| 1-Pentene, perfluoro | 250.04 | 29.0 | 3 |
| 1-Butyne, 3-methyl | 68.12 | 29.5 | 1 |
| 1-Pentene | 70.13 | 30.0 | 1 |
| 1-Pentene, 3,3,4,4,5,5,5-heptafluoro | 196 | 30.0 | 3 |
| Ethylene, idotrifluoro | 207.9 | 30.0 | 3 |

Chemical List: Boiling Points in degrees Celcius

| Chemical Name | Molecular Weight | Boiling Point | Chemical Group |
|---|---|---|---|
| Styrene, 3-fluoro | 122.14 | 30.0 | 11 |
| 1-Pentene, 3-bromo | 149.03 | 30.5 | 3 |
| Pentane, perfluoro | 288.04 | 30.5 | 3 |
| Ethane, 1,2-trifluoro | 66.05 | 30.7 | 3 |
| Butane, 3-methyl, 1,1,1-trifluoro | 126.12 | 31.0 | 3 |
| 1-Butene, 2-methyl | 70.13 | 31.2 | 1 |
| Formic acid, methyl ester | 60.05 | 31.5 | 9 |
| Methane sulfonyl chloride, trifluoro | 168.52 | 31.6 | 3 |
| Ethane, 1,1-dichloro-1-fluoro | 116.95 | 32.0 | 3 |
| Pentane, 1-fluoro | 90.14 | 32.0 | 3 |
| Acetylene-diido | 277.83 | 32.0 | 3 |
| Propane, 2-amino | 59.11 | 32.4 | 10 |
| Butane, 1-fluoro | 76.11 | 32.5 | 3 |
| Methyl isopropyl ether | 74.12 | 32.5 | 6 |
| Propylene, 1-chloro | 76.53 | 32.8 | 3 |
| Butyraldehyde, 2-bromo | 151 | 33.0 | 3 |
| 2-Butene, 2-chloro-1,1,1,4,4,4-hexafluoro | 198.5 | 33.0 | 3 |
| 1,3-Butadiene, 1,2,3-trichloro | 157.43 | 33.0 | 3 |
| Butene, 2-chloro-1,1,1,4,4,4-hexafluoro | 199 | 33.0 | 3 |
| bis-(Dimethyl phosphino) amine | 137.1 | 33.5 | 10 |
| 1,3-Butadiene, 2-methyl | 68.12 | 34.0 | 1 |
| 1-Butene-3-yne, 2-methyl | 66.1 | 34.0 | 1 |
| Isoprene | 68.12 | 34.0 | 1 |
| Methane, chloro dinitro | 140.48 | 34.0 | 3 |
| Propane, 1,2-epoxy | 58.08 | 34.3 | 6 |
| Cyclopropane, ethyl | 70.13 | 34.5 | 1 |
| Ethyl ether | 74.12 | 34.5 | 6 |
| Dimethyl disulfide, hexafluoro | 202.13 | 34.6 | 11 |
| Ethylene, 1,2-chloro-1-fluoro | 115 | 35.0 | 3 |
| Propane, 1,2-dichlorohexafluoro | 220.93 | 35.0 | 3 |
| Ethyl vinyl ether | 72.11 | 35.0 | 6 |
| Propane, 2-chloro | 78.54 | 35.7 | 3 |
| Methane, bromo-chloro-fluoro | 147.37 | 36.0 | 3 |
| Piperidine, 2,3,6-trimethyl | 127.23 | 36.0 | 11 |
| 1,2,3-Nonadecane tricarboxylic acid, 2-hydroxy, trimethylester | 500.72 | 36.0 | 9 |
| Dimethyl ethyl amine | 73.14 | 36.0 | 10 |
| n-Pentane | 72.15 | 36.1 | 1 |
| 2-Pentene {trans} | 70.13 | 36.3 | 1 |
| Cyclobutane, methyl | 70.13 | 36.3 | |
| Ethyl methyl amine | 59.11 | 36.7 | 10 |
| 2-Pentene {cis} | 70.13 | 36.9 | 1 |
| Cyclopropane 1,2-dimethyl {cis} | 70.13 | 37.0 | 1 |
| Ethylene, 1,1-dichloro | 96.94 | 37.0 | 3 |
| Propylene, 1-chloro-{trans} | 76.53 | 37.4 | 3 |
| Ethylene, 1,1-chloro-2-fluoro | 14.93 | 37.5 | 3 |
| Methane, dichloro | 84.93 | 40.0 | 3 |
| Methane, iodo- | 141.94 | 42.4 | 3 |
| Ethane, 1,1-dichloro | 98 | 57.3 | 3 |

CHEMICAL GROUP DESIGNATION
1 Aliphatic hydrocarbons and/or derivatives
2 Aromatic hydrocarbons and/or derivatives
3 Organic halides and/or derivatives
6 Ethers and/or derivatives
7 Aldehydes and/or derivatives
9 Carboxylic acids and/or derivatives
10 Amines and/of derivatives
11 Miscellaneous

EXAMPLE 46

The dispersed phase can also be selected from a group of azeotropes by the principles and criteria as set down in Example 45. A listing of some, but not all binary azeotropes, with the boiling points follows:

Acetone (21%)-Pentane (79%) 32° C.; Ethyl ether (48%)-Isoprene (52%) 33° C.; Ethyl ether (44%)-methyl for XXX (56%) 28° C.; Ethyl ether (98.8%)-Water (1.2%) 34° C.; Isoprene (86%)-2-methyl-2-butane (14%) 34° C.; Isopropyl chloride (99%)-Water (1%) 35° C.; Methyl vinyl chloride (99.1%)-Water (0.9%) 33° C.; Pentane (98.6%)-Water (1.4%) 34° C.; Vinyl ethyl ether (98.5%)-Water (1.5%) 34° C.

A listing of some but not all ternary azeotropes, with the boiling point follows:

Acetone (7.6%)-Isoprene (92%)-Water (0.4%) 32° C.; Carbon disulfide (4/XXX(46.2%)-Methanol (64.7%)-Methyl acetate (57%) 37° C.: Carbon disulfide (55%)-Methanol (7%)-Methylal (38%) 35° C.;

EXAMPLE 47

The colloidal dispersions of the present invention are distinct and differ from prior art emulsions for ultrasound contrast in that at least some portion of the dispersed phase percolates or vaporizes following administration to an organism. The presence of this dispersed material with a distinct liquid-gas interface provides the basis for the strong backscatter of the acoustic beam.

One test of the presence of a dispersed gas phase emulsion is the response of the ultrasound backscatter from the dispersion to changes in pressure. While true liquid dispersions are largely insensitive to compressive forces, a gaseous colloidal dispersion will show a decrease in acoustic backscatter when pressure is applied, due to compression of the gas and a decrease in the effective backscatter cross section.

With the experimental system of Example 1, the acoustic backscatter in a sealed beaker was tested through an acoustic window. Then pressure was applied to the system and rerecording the acoustic backscatter recorded. Since the acoustic backscatter differed significantly following the application of pressure it was concluded that the dispersed phase contains some portion in the gas state.

EXAMPLE 48

A formulation of the present invention can be made by condensation of the dispersed phase from the gas state rather than comminution from the liquid state and involves the following equipment and steps: Microfluidizer, Model 110Y, Interaction chamber pressure 14,000 PSI; Pressure vessels, 316 steel, 5 L and 12 L sizes; Filters, cellulose acetate, 0.22 micron; Filter holders, 142 mm. The following solutions were made: 36% iohexol, 10 L; 41.75 g Pluronic P-123, 41.75 g Zonyl FSO, 2.5 L, sonicate to aid dissolution (stock surfactant solution). The Microfluidizer was primed with the iohexol solution and the entire container cooled to −6° C. The interaction chamber, tubing, and cooling coil are covered with chipped ice during the condensation process. To a 5 L pressure vessel with stir bar in an ice bath add 1800 mL stock surfactant solution. A tank of propane (boiling point −42° C.) was attached to the interaction chamber by gas tight fittings and the chamber charged with 200 g of propane. The entire vessel was pressurized to 10 PSI with nitrogen for 45 min while stirring. The suspension was passed through the Microfluidizer for 30 min at 5,000 PSI for 60 min at 14,000 PSI. The emulsion was transferred to a vessel containing 8 L of water at 4° C. and mixed well and transferred to 100 mL vials using positive pressure, passing the material through a 0.22 micron filter in the process. Cap and seal the vials.

Other emulsions containing other low boiling materials of Example 45 can be made in a similar manner by varying the dispersed phase and being certain the pressure and temperature are sufficient to liquify the dispersed phase material.

EXAMPLE 49

The dispersed phase can be composed of any chemical which has a boiling point under standard pressure conditions below the body temperature of the organism to which the formulation is to be administered and which will be examined following administration by ultrasound. Example 45 discusses how one selects suitable chemicals for the dispersed phase based on the temperature range obtained by consideration of the boiling point of the selected chemical and parameters of the manufacturing process.

Having determined that the boiling point under standard conditions of pressure is preferably below approximately 37° C., it has been found that selecting chemicals by the total number of atoms present provides an alternative method of selecting suitable materials as ultrasound contrast agents. A listing of suitable chemicals, arranged by total atoms present, reveals that all preferred chemicals contain between four and seventeen atoms and follows:

Chemical List Boiling Points in degrees Celcius

| Name | Total Atoms | Molecular Formula | Molecular Weight | Boiling Point |
| --- | --- | --- | --- | --- |
| bromo-methane | 4 | CH3Br | 94.94 | 3.2 |
| bromo-difluoro-methane | 5 | CHBrF2 | 130.92 | −14.15 |
| chloro-fluoro-methane | 5 | CH2ClF | 68.48 | −9.15 |
| bromo-trideuterio-methane | 5 | CD3Br | 12 | 2.8 |
| propadienedione | 5 | C3O2 | 68.03 | 6.8 |
| dicholoro-fluoro-methane | 5 | CHCl2F | 102.92 | 8.9 |
| methaneselenol | 5 | CH4Se | 95 | 12 |
| difluoro-iodo-methane | 5 | CHF2I | 177.92 | 21.6 |
| dibromo-difluoro-methane | 5 | CBr2F2 | 209.82 | 22.79 |
| trichloro-fluoro-methane | 5 | CCl3F | 137.7 | 23.65 |
| bromo-chloro-fluoro-methane | 5 | CHBrClF | 147.37 | 36.11 |
| 2-chloro- 1,1-difluoro-ethene | 6 | C2HClF2 | 98.48 | −18.6 |
| trifluoro-methaneselenol | 6 | CHF3Se | 148.97 | −14.5 |
| chloro-ethene | 6 | C2H3Cl | 62.5 | −13.9 |
| oxalyl fluoride | 6 | C2F2O2 | 94.02 | −2.7 |
| formamide | 6 | CH3NO | 45.04 | 2.18 |
| 2-bromo- 1,1-difluoro-ethene | 6 | C2HBrF2 | 142.93 | 5.7 |
| methanethiol | 6 | CH4S | 48.1 | 5.9 |
| butadiyne | 6 | C4H2 | 50.06 | 9 |
| bromo-ethene | 6 | C2H3Br | 106.95 | 15.6 |
| 1,1- dichloro-2,2-difluoro-ethene | 6 | C2Cl2F2 | 132.92 | 18.9 |
| trans-1- bromo-2-fluoro-ethylene | 6 | C2H2BrF | 124.94 | 19.8 |
| bromo-methane | 4 | CH3Br | 94.94 | 3.2 |
| 1,1- dichloro-2,2-difluoro-ethene | 6 | C2Cl2F2 | 132.92 | 20 |
| 1,1 dichloro-ethene | 6 | C2H2Cl2 | 96.94 | 31.8 |
| trans-1,2 Dichlorfluoroethylene | 6 | C2HCl2F | 114.93 | 37 |
| cis Dichlorofluoroethylene | 6 | C2HCl2F | 114.93 | 37 |
| 1,1 dichloro-2-fluoro-ethene | 6 | C2HCl2F | 14.93 | 37 |
| Methyldifluoramine | 7 | CH3F2N | 67.02 | −16 |
| difluorophosphoric acid methyl ester | 7 | CH3F2OP | 100 | −15.5 |
| methylamine | 7 | CH5N | 31.06 | −6.5 |
| dichloro-methyl-borane | 7 | CH3BCl2 | 96.75 | 11.5 |

Chemical List Boiling Points in degrees Celcius

| Name | Total Atoms | Molecular Formula | Molecular Weight | Boiling Point |
|---|---|---|---|---|
| tetrachloro-1,2-difluoro-ethane | 8 | C2Cl4F2 | 203.83 | −37.5 |
| 1,1,2- trichloro-ethane | 8 | C2H3Cl3 | 133.4 | −24 |
| 1,1,1,2- tetrachloro-ethane | 8 | C2H2Cl4 | 167.85 | −16.3 |
| 1-chloro- 1,1-difluoro-ethane | 8 | C2H3ClF2 | 100.5 | −9.8 |
| 1,2- dibromo-1,1-dichloro-ethane | 8 | C2H2Br2Cl2 | 256.75 | 1.78 |
| 1,1- dichloro-tetrafluoro-ethane | 8 | C2Cl2F4 | 170.92 | 3 |
| 1,1,2- trifluoro-ethane | 8 | C2H3F3 | 84.04 | 3 |
| 1,2- dichloro-tetrafluoro-ethane | 8 | C2Cl2F4 | 170.92 | 3.5 |
| Tetrafluor-(methyl-methylamine) | 8 | C2HF4N | 115.03 | 5 |
| butenyne | 8 | C4H4 | 52.08 | 5.11 |
| 2-chloro- 1,1,1-trifluo-ethane | 8 | C2H2ClF3 | 118.49 | 6 |
| Fluorcarbonyl-trifluormethyl-sulfane | 8 | C2F4OS | 148.08 | 8 |
| chloro-methyl-silane | 8 | CH5ClSi | 80.59 | 8 |
| 1,2- difluoro-ethane | 8 | C2H4F2 | 66.05 | 10 |
| chloro-ethane | 8 | C2D5Cl | 64.51 | 12 |
| pentafluoro-iodo-ethane | 8 | C2F5I | 245.92 | 12.5 |
| 2- diazo-1,1,1-trifluoro-ethane | 8 | C2HF3N2 | 110.04 | 13 |
| 1-chloro 1-fluoro-ethane | 8 | C2H4ClF | 82.31 | 16 |
| 1,1,2- tetrachloro-ethane | 8 | C2H2Cl4 | 167.85 | 16.3 |
| 1,12- trichloro-ethane | 8 | C2H3Cl3 | 133.4 | 24 |
| 2- bromo-1,1,1-trifluoro-ethan | 8 | C2H2BrF3 | 162.94 | 26 |
| Chlormethyl-trifluor-silane | 8 | CH2ClF3Si | 134.56 | 26 |
| 1,2- difluoro-ethane | 8 | C2H4F2 | 66.05 | 30.7 |
| 2- chloro-1,1-difluoro-ethane | 8 | C2H3ClF2 | 100.05 | 35.1 |
| tetrachloro-1,2-difluoro-ethane | 8 | C2Cl4F2 | 203.83 | 37.5 |
| bromo-pentadeuterio-ethane | 8 | C2BrD5 | 114 | 38 |
| dimethyl-silane | 9 | C2H8Si | 60.1 | −20 |
| Pentafluor-cyclopropane | 9 | C3HF5 | 132.03 | −9 |
| difluoromethyl-trifluoromethyl sulfide | 9 | C3HF5S | 152.08 | 0.8 |
| 1,1,2,3,3- pentafluoro-propene | 9 | C3HF5 | 132.03 | 1.8 |
| Chlorpentafluorcyclopropane | 9 | C3ClF5 | 166.48 | 3 |
| Germylacetylene | 9 | C2H4Ge | 100.64 | 3.85 |
| rans-1,1,2,3 Tetrafluorcyclopropane | 9 | C3H2F4 | 114.04 | 6 |
| 2- chloro-pentafluoro-propene | 9 | C3ClF5 | 166.48 | 6.7 |
| 3- chloro-pentafluoro-propene | 9 | C3ClF5 | 166.48 | 7.3 |
| 1- chloro-pentafluoro-propene | 9 | C3ClF5 | 166.48 | 8 |
| fluoro-methyl-methyl ether | 9 | C2H5FO | 64.06 | 19 |
| Brompentafluorcyclopropane | 9 | C3BrF5 | 210.93 | 20.5 |
| Vinyloxy-acetylene | 9 | C4H4O | 68.08 | 22 |
| 2- chloro-propene | 9 | C3H5Cl | 76.53 | 22.6 |
| cis-trans-1- Chlor-1,2,2,3-tetrafluorcyklopropane | 9 | C3HClF4 | 148.49 | 24.5 |
| 3- bromo-pentafluoro-propene | 9 | C3BrF5 | 210.93 | 26.5 |
| 2,2- dichloro-1,1,1-trifluoro-ethane | 9 | C2HCl3F3 | 152.93 | 27 |
| Furan | 9 | C4H4O | 68.08 | 31 |
| 1- chloro-propene | 9 | C3H5Cl | 76.53 | 32.1 |
| 2- Chlor-vinyl-trifluorsilane | 9 | C2H2ClF3Si | 146.57 | 33 |
| cis-1,1,2,3 Tetrafluorcyclopropane | 9 | C3H2F4 | 114.04 | 34 |
| 3- bromo-1,1,3,-tetrafluoro-propene | 9 | C3HBrF4 | 192.94 | 34 |
| ethanethiol | 9 | C2H6Si | 62.13 | 35 |
| dimethyl sulfide | 9 | C2H6S | 62.13 | 36 |
| ( chloro-fluoro-methyl)-trifluoromethyl sulfide | 9 | C2HClF4S | 168.54 | 37 |
| 1 t- chloro-propane | 9 | C3H5Cl | 76.53 | 37.2 |
| buta-1,3-diene | 10 | C4H6 | 54.09 | −4.6 |
| 1,5- Dicarbaclosotriborane | 10 | C2H5B3 | 61.49 | −3.7 |
| omega- Nitrosoperfluorpropionnitrile | 10 | C3F4N2O | 156.04 | 2 |
| pentafluoro-propionaldehyde | 10 | C3HF5O | 148.03 | 2 |
| 1,1- difluoro-buta-1,3-diene | 10 | C4H4F2 | 90.07 | 3.5 |
| methyl-vinyl ether | 10 | C3H6O | 58.08 | 5 |
| hexafluoro-buta-1,3-diene | 10 | C4F6 | 162.03 | 5.8 |
| but-1-yne | 10 | C4H6 | 54.09 | 7.9 |
| 1-Deutero-1-butane | 10 | C4H5D | 55.1 | 8 |
| methylene-cyclopropane | 10 | C4H6 | 54.09 | 8.8 |
| buta-1,2-diene | 10 | C4H6 | 54.09 | 10.84 |
| 2- fluoro-buta-1,3-diene | 10 | C4H5F | 72.08 | 11.5 |
| 1H- pentafluoro-but-1-yne | 10 | C4HF5 | 144.04 | 12 |
| pentafluoro-acetone | 10 | C3HF5O | 148.03 | 13.5 |
| Difluoraminoethane | 10 | C2H5F2N | 81.07 | 14.9 |
| Tetra-B-fluor-B,B'-ethenediyl-bis-borane | 10 | C2H2B2F4 | 123.65 | 15 |
| cis-1- Fluor-1,3-butadiene | 10 | C4H5F | 72.08 | 15.6 |
| trans-1- Flour-1,3-butadiene | 10 | C4H5F | 72.08 | 16 |
| ethylamine | 10 | C2H7N | 45.08 | 16.6 |
| dimethyl-phosphine | 10 | C2H7P | 62.05 | 20 |
| N- Methyl-imino-schwefel-tetra-fluoride | 10 | CH3F4NS | 137.1 | 21.8 |

Chemical List Boiling Points in degrees Celcius

| Name | Total Atoms | Molecular Formula | Molecular Weight | Boiling Point |
|---|---|---|---|---|
| Methylschwefelpentafluoride | 10 | CH3F5S | 142.09 | 26 |
| but-2-yne | 10 | C4H6 | 54.09 | 26.97 |
| bromo-pentafluoro-acetone | 10 | C3BrF5O | 226.93 | 31 |
| bromo-dimethyl-borane | 10 | C2H6BBr | 120.78 | 31.75 |
| 1- chloro-2,3,3,4,4-pentanfluoro-cyclobutene | 10 | C4ClF5 | 178.49 | 33 |
| bis- trifluoromethyl disulfide | 10 | C2F6S2 | 202.13 | 34 |
| (±)(1)1,2- epoxy-propane | 10 | C3H6O | 58.08 | 34.23 |
| ethyl-silane | 11 | C2H8Si | 60.17 | −14 |
| 1,1,1- trifluoro propane | 11 | C3H5F3 | 98.07 | −13 |
| 2- fluoro-propane | 11 | C3H7F | 62.09 | −11 |
| Perfluormethoxyacetylfluoride | 11 | C3F6O2 | 182.02 | −9.7 |
| ethyl-trifluoro-silane | 11 | C2H5F3Si | 114.14 | −4.4 |
| 1- fluoro-propane | 11 | C3H7F | 62.09 | −3 |
| 2,2- difluoro-propane | 11 | C3H6F2 | 80.08 | −0.6 |
| 1,1,1,3,3,3-hexafluoro-propane | 11 | C3H2F6 | 152.04 | −0.5 |
| Perfluorcyclobutanone | 11 | C4F6O | 178.03 | 1 |
| 1,1,1,2,2,3-hexafluoro-propane | 11 | C3H2F6 | 152.04 | 1.2 |
| 2- chloro-heptafluoro-propane | 11 | C3ClF7 | 204.47 | 2.2 |
| dideuterio-dimethyl germane | 11 | C2H6D2Ge | 106.69 | 6.5 |
| 1,1- difluoro-propane | 11 | C3G6F2 | 80.08 | 7 |
| ethyl-trideuterio germane | 11 | C2H5D3Ge | 107.69 | 11.3 |
| disilanyl-methane | 11 | CH8Si2 | 76.25 | 14 |
| 1-chloro- 1,1,2,2-tetrafluoro-propane | 11 | C3H3ClF4 | 150.5 | 19.93 |
| Trifluorosilydimethylamine | 11 | C2H6F3NSi | 129.16 | 21 |
| ethylidene-methyl-amine | 11 | C3H7N | 57.1 | 27.5 |
| disilanyl-methane | 11 | CH8Si2 | 76.25 | 28 |
| divinyl ether | 11 | C4H6O | 70.09 | 28 |
| 1,1,1,3- tetrafluoro-propane | 11 | C3H4F4 | 116.06 | 29.4 |
| 1- Sila-3-germapropane | 11 | CH8GeSi | 120.75 | 30 |
| 2- chloro-1,1,1-trifluoro-propane | 11 | C3H4ClF3 | 132.51 | 30 |
| 2- methyl-but-1-en-3-yne | 11 | C5H6 | 66.1 | 32 |
| Bis-trifluorsilyldichlormethane | 11 | CCl2F6Si2 | 253.08 | 34 |
| 1,2- dichlorohexafluoro-propane | 11 | C3Cl2F6 | 220.93 | 34.8 |
| 2- chloro-propane | 11 | C3H7Cl | 78.54 | 34.8 |
| ethyl-vinyl ether | 11 | C2H8O | 72.11 | 35 |
| 3- methylen-oxetane | 11 | C4H6O | 70.09 | 35 |
| 2- chloro-fluoro-propane | 11 | C3H6ClF | 96.53 | 35.2 |
| Bis- trifluorsilylmethan | 11 | CH2F6Si2 | 184.19 | 35.5 |
| chloro-dimethyl-silane | 11 | C2H7ClSi | 94.62 | 35.7 |
| 1,3 dichloro-hexafluoro-propane | 11 | C3Cl2F6 | 220.93 | 36.1 |
| Bis-trifluorsilylchlormethane | 11 | CHClF6Si2 | 218.63 | 37 |
| heptafluoro-1-nitro-propane | 12 | C3F7NO | 199.03 | −9.5 |
| 1,1,2,2,3- pentafluoro-3-trifluoromethyl-cyclopropane | 12 | C4F8 | 200.03 | −9 |
| 2- methyl-propene | 12 | C4H8 | 56.11 | −6.9 |
| octafluoro-cyclobutane | 12 | C4F8 | 200.03 | −6.42 |
| but-1-ene | 12 | C4H8 | 56.11 | −6.3 |
| 1,1,2,2- Tetrafluor-2-trifluoromethoxy-aethane | 12 | C3HF7O | 186.03 | −2 |
| cis-octafluoro-butene-(2) | 12 | C4F8 | 200.03 | 0.4 |
| methyl-cyclopropane | 12 | C4H8 | 56.11 | 0.7 |
| but-2 t-ene | 12 | C4H8 | 56.11 | 0.88 |
| butene-(2) | 12 | C4H8 | 56.11 | 1 |
| heptafluoro-butyronitrile | 12 | C4F7N | 195.04 | 1 |
| octafluoro-but-2-ene | 12 | C4F8 | 200.03 | 12 |
| 1,1- difluoro-but-1-ene | 12 | C4H6F2 | 92.09 | 3.71 |
| but-2 c-ene | 12 | C4H8 | 56.11 | 3.72 |
| octafluoro-but-1-ene | 12 | C4F8 | 200.03 | 4.8 |
| 1,1,1,4,4,4-Hexafluor-2-butene | 12 | C4H2F6 | 164.05 | 5.4 |
| trifluormethylethylether | 12 | C3H5F3O | 114.07 | 5.5 |
| 2H,3H- hexafluoro-but-2 t-ene | 12 | C4H2F6 | 164.05 | 6 |
| 3,3,3- trifluoro-2-methyl-propene | 12 | C4H5F3 | 110.08 | 6 |
| ethyl-methyl ether | 12 | C3H8O | 60.1 | 6.6 |
| 2H- Heptafluor-buten-(1) | 12 | C4HF7 | 182.04 | 10 |
| cyclobutane | 12 | C4H8 | 56.11 | 12 |
| pentafluoro-2-methyl-propene | 12 | C4H3F5 | 146.06 | 12.8 |
| Methyl-vinylsilane | 12 | C3H8Si | 72.18 | 13.7 |
| 1,1,1- trifluoro-but-2 t-ene | 12 | C4H5F3 | 110.05 | 20 |
| 1,1,1- trifluoro-but-2 t-ene | 12 | C4H5F3 | 110.08 | 20 |
| Allyltrifluorsilane | 12 | C3H5F3Si | 126.15 | 21 |
| 1,1,2 Trifluor-2-trifluormethylcyclopropane | 12 | C4H2F6 | 164.05 | 21.5 |
| 1,1,2- Trifluor-1-chlor-2-trifluormethoxy-aethane | 12 | C3HClF6O | 202.48 | 23 |
| heptafluoro-propane-1-thiol | 12 | C3HF7S | 202.9 | 23.7 |

Chemical List Boiling Points in degrees Celcius

-continued

| Name | Total Atoms | Molecular Formula | Molecular Weight | Boiling Point |
|---|---|---|---|---|
| (2- Brom-1,1,2,2-tetrafluor-ethyl)-trifluormethyl-ether | 12 | C3BrF7O | 264.93 | 24 |
| Cyclopropylsilane | 12 | C3H8Si | 72.18 | 26.8 |
| 3,3 difluoro-2-methyl-propene | 12 | C4H6F2 | 92.09 | 28.1 |
| 1,1,2,2- Tetrafluorethyldifluormethylether | 12 | C3H2F6O | 168.04 | 28.5 |
| 2,2,2 Trifluorethyl-difluormethylether | 12 | C3H3F5O | 150.05 | 29 |
| 1,1,1- trifluoro-2-methoxy-ethane | 12 | C3H5F3O | 114.07 | 31 |
| 2- chloro-heptafluoro-but-2-ene | 12 | C4ClF7 | 216.49 | 32.2 |
| Pentafluoronitroacetone | 12 | C3F5NO3 | 193.03 | 32.6 |
| 2H,3H hexafluoro-but-2 cene | 12 | C4H2F6 | 164.05 | 33.2 |
| 2- chloro-3H-hexafluoro-but-2-ene | 12 | C4HClF6 | 198.5 | 34.4 |
| tetra-B-fluoro-B,B'-ethanediyl-bis-borane | 12 | C2H4B2F4 | 125.67 | 35 |
| Ethyl-trifluormethyl-sulfide | 12 | C3H5F3S | 130.13 | 35 |
| methyl-(1,1,2,2-tetrafluoro-ethyl)-ether | 12 | C3H4F4O | 132.06 | 36.5 |
| (Chlor-difluormethyl)-(2,2,2-trifluor-ethyl)-ether | 12 | C3H2ClF5O | 184.49 | 37 |
| 1,1,2- Trifluor-1,2-dichlor-2-trifluormethoxy-aethane | 12 | C3Cl2F6O | 236.93 | 37 |
| 1-Nitroso-2-trifluormethoxy-tetrafluorethane | 13 | C3F7NO2 | 215.03 | −10.3 |
| Nonafluor-2-azabutane | 13 | C3F9N | 221.03 | −3.8 |
| trimethyl-amine | 13 | C3H9N | 59.11 | 3.5 |
| 3,3- Dimethyl-cyclopropene | 13 | C5H8 | 68.12 | 18 |
| penta-1,4-diene | 13 | C5H8 | 68.12 | 24 |
| 3- methyl-but-1-yne | 13 | C5H8 | 68.12 | 26 |
| 3- Methyl-cyclobutene | 13 | C5H8 | 68.12 | 27.5 |
| Trifluormethanazo-2,2,2-trifluoraethane | 13 | C3H2F6N2 | 180.05 | 28 |
| 2- methyl-buta-1,3-diene | 13 | C5H8 | 68.12 | 30 |
| alpha-Nitroso-perfluorisobutryronitrile | 13 | C4F6N2O | 206.05 | 31 |
| isopropylamine | 13 | C3H9N | 59.11 | 31.7 |
| 2- Methoxyperfluoropropene | 13 | C4H3F5O | 162.06 | 32 |
| Dimethylethinylsilane | 13 | C4H8Si | 84.19 | 32 |
| 1,1,2,2- Tetradeuterospiropentane | 13 | C5H4D4 | 72.14 | 33 |
| dimethoxy-silane | 13 | C2H8O2Si | 92.17 | 33.5 |
| isopropenyl-methyl ether | 13 | C4H8O | 72.11 | 34 |
| tert-butyl-silane | 13 | C4H12Si | 88.22 | 34.4 |
| spiropentane | 13 | C5H8 | 68.12 | 35 |
| 3,4,4- Trifluorisoprene | 13 | C5H5F3 | 122.09 | 35 |
| 1- methyl-cyclobutene | 13 | C5H8 | 68.12 | 37 |
| 2- methyl-propane | 14 | C4H10 | 58.12 | −13.3 |
| decafluoro-butane | 14 | C4F10 | 238.03 | −1.7 |
| 1- deuterio-butane | 14 | C4H9D | 59.13 | −0.5 |
| butane | 14 | C4H10 | | −0.5 |
| Perfluorethoxyacetylfluoride | 14 | C4F8O2 | 232.3 | 0 |
| trimethyl-silane | 14 | C3H10Si | 74.2 | 6.7 |
| Trifluormethylpentafluor-2-oxapropylketone | 14 | C4F8O2 | 232.03 | 8 |
| 2-fluoro- 2-methyl-propane | 14 | C4H9F | 76.11 | 11 |
| pentafluoroethyl-tetrafluoroethyliden-amine | 14 | C4F9N | 233.04 | 12.8 |
| 2- Trifluoromethyl-propane | 14 | C4H7F3 | 112.09 | 13 |
| Perfluor-2-aza-penten(2) | 14 | C4F9N | 233.04 | 13.2 |
| fluoro-trimethyl-silane | 14 | C3H9FSi | 92.19 | 16 |
| 1,1,1- trifluoro-butane | 14 | C4H7F3 | 112.09 | 16.74 |
| dimethyl-vinyl-borane | 14 | C4H9B | 67.93 | 17.1 |
| Tris-(trifluoromethyl)-germaniumfluoride | 14 | C3F10Ge | 298.61 | 19.1 |
| fluoro-trimethyl-silane | 14 | C3H9FSi | 92.19 | 20 |
| propyl-silane | 14 | C3H10Si | 74.2 | 21.3 |
| 1,1,1,3,3,3-hexafluoro-2-methyl-propane | 14 | C4H4F6 | 166.07 | 21.5 |
| 2- fluoro-butane | 14 | C4H9FF | 76.11 | 24 |
| 1,1,1,4,4,4-hexafluoro-butane | 14 | C4H4F6 | 166.07 | 24.5 |
| methoxy-dimethyl-borane | 14 | C3H9BO | 71.91 | 24.6 |
| trifluoro-propyl-silane | 14 | C3H7F3Si | 128.17 | 25 |
| Deuterio-trimethyl germane | 14 | C3H9DGe | 119.71 | 26 |
| Trimethyl Germane | 14 | C3H10Ge | 118.7 | 26 |
| trimethyl-hydroxylanine | 14 | C3H9NO | 75.11 | 30 |
| 2,2 difluoro-butane | 14 | C4H8F2 | 94.1 | 30.92 |
| 1- fluoro-butane | 14 | C4H9F | 76.11 | 31 |
| Tris- (trifluorormethyl)-germaniumchloride | 14 | C3ClF9Ge | 315.06 | 37 |
| nonafluoro-1-nitroso-butane | 15 | C4F9NO | 249.04 | 16 |
| 3 methyl-but-1-ene | 15 | C5H10 | 70.13 | 20 |

-continued

Chemical List Boiling Points in degrees Celcius

| Name | Total Atoms | Molecular Formula | Molecular Weight | Boiling Point |
|---|---|---|---|---|
| 1,1- dimethyl-cyclopropane | 15 | C5H10 | 70.13 | 20 |
| 3- methyl-but-1-ene | 15 | C5H10 | 70.13 | 20 |
| 1,1- dimethyl-cyclopropane | 15 | C5H10 | 70.13 | 20.6 |
| decafluoro-cyclopentane | 15 | C5F10 | 250.04 | 22.48 |
| 1,1,1,3,3,3-Hexafluoro-2-nitroso-2-trifluoromethyl-propane | 15 | C4F9NO | 249.04 | 24 |
| ± Trans-1,2-dimethyl-cyclopropane | 15 | C5H10 | 70.13 | 28.2 |
| 1,2 dimethyl-cyclopropane | 15 | C5H10 | 70.13 | 28.8 |
| pent-1-ene | 5 | C5H10 | 70.13 | 29 |
| 1- Nitroso-4-monohydrooctafluorbutane | 15 | C4HF8NO | 231.05 | 30 |
| trifluoro-acetic acid- (bis-trifluoromethyl-amide) | 15 | C4F9NO | 249.04 | 30 |
| isopropyl-methyl ether | 15 | C4H10O | 74.12 | 30.77 |
| 2- methyl-but-1-ene | 15 | C5H10 | 70.13 | 30.95 |
| Perfluorpropylmethylether | 15 | C4H3F7O | 200.06 | 34 |
| diethyl ether | 15 | C4H10O | 74.12 | 34.6 |
| ethyl-cyclopropane | 15 | C5H10 | 70.13 | 35.8 |
| methyl-cyclobutane | 15 | C5H10 | 70.13 | 36 |
| pent-2-ene | 15 | C5H10 | 70.13 | 36.15 |
| pent-2-ene | 15 | C5H10 | 70.13 | 36.55 |
| cis-1,2- dimethyl-cyclopropane | 15 | C5H10 | 70.13 | 37.03 |
| 2- methyl-but-2-ene | 15 | C5H10 | 70.13 | 37.2 |
| beta- Nitroso-nonafluordiethylether | 16 | C4F9NO2 | 265.04 | 15 |
| nitrous acid ethyl ester | 16 | C2H5NO2 | 75.07 | 17.4 |
| Perfluor-diethylamine | 16 | C4F11N | 271.03 | 23.9 |
| Perfluor-2-aza-pentan | 16 | C4F11N | 271.03 | 24.3 |
| 4- Methylpent-4-ensaeurenitrile | 16 | C6H9N | 95.14 | 30 |
| butyl-fluoro-borane | 16 | C4H9BF2 | 105.92 | 35 |
| ethyl-dimethyl-amine | 16 | C4H11N | 73.14 | 36.4 |
| 3,3 dimethyl-but-1-yne | 16 | C6H10 | 82.15 | 37 |
| 2,2- dimethyl-propane | 17 | C5H12 | 72.15 | 0.95 |
| (−)(S)-1- fluoro-2-methyl-butane | 17 | C5H11F | 90.14 | 14.1 |
| (−)(R)-2- chloro-pentaine | 17 | C5H11Cl | 106.59 | 24.7 |
| Tetramethyl-stannane | 17 | C4H12Sn | 178.53 | 26 |
| 2- methyl-butane | 17 | C5H12 | 72.15 | 27.55 |
| nonafluoro-2-trifluoromethyl-butane | 17 | C5F12 | 288.04 | 30.12 |
| Tetrakis(trifluoromethyl) germane | 17 | C4F12Ge | 345.61 | 31.7 |
| pentane | 17 | C5H12 | 72.15 | 36 |

EXAMPLE 50

In a preferred embodiment, the dispersed phase can be composed of any chemical which has a boiling point under standard pressure conditions below the body temperature of the organism to which the formulation is to be administered and which will be examined following administration by ultrasound. Example 45 discusses how one selects suitable chemicals for the dispersed phase based on the temperature range obtained by consideration of the boiling point of the selected chemical and parameters of the manufacturing process.

The boiling of pentane (dodecahydropentane) and perfluoropentane (Dodecafluoropentane) are 36°–37° C. and 28°–29° C., respectively. This is an excellent temperature range in which to select suitable chemicals as the dispersed phase. Therefore, chemicals which contain five carbon atoms and variable hydrogen and fluorine atoms will have boiling points between 28° and 37° C. and will make suitable dispersed phase chemicals. The following listing of suitable chemicals contains some, but not all chemicals containing five carbons, with variable numbers of hydrogen and fluorine atoms, i.e., $C_5H_xF_y$:

1,3-Cyclopentadiene, 5,5-difluoro-;Cyclobutane, 1-fluoro-3-methylene-;2H-Fluorinium; Cyclobutane, (fluoromethylene)-; Methylene, cyclobutylfluoro-; 2,4-Cyclopentadien-1-yl, 2-fluoro-; 2H-Fluorinium, ion(−1), (deloc-2,3,4,5,6)-; 6-Fluoroniabicyclo(3.1.0) hexane; 6-Fluoroniabicyclo(3.1.0)hex-2-ene, hydroxide, inner salt; Fluorine(2+),1,3-pentadien-1-yl-5-ylidene-; 1,3-Pentadiene, fluorine complex; Fluoranium; Cyclopentyne, 4-fluoro-; Cyclobutene, 3-(trifluoromethyl)-; Cyclopentane, 1,1,2,2,3,3-hexafluoro-; Tricyclo(1.1.1.01,3)pentane, fluoro-, ion (1−); Spiro(2.2)pentane, fluoro-, ion(−1); Tricyclo (1.1.1.01.3)pentane, fluoro-; cyclopentane, 1,2-difluoro-, trans-; Cyclobutane, 1,1-difluoro-3-methylene; 1,3-Cyclopentadiene, 2-fluoro-; 1,3-Cyclopentadiene, 1-fluoro-; Bicyclo(1.1.1)pentane, 1,3-difluoro-; 1,3-Cyclopentadiene, 1,2,3,4,5-pentafluoro-, dimer; 1,3-Cyclopentadiene, 1,2,3,4-tetrafluoro; 1,3-Cyclopentadiene, 1,2,3,4,5-pentafluoro-; Cyclopentene, 1,2,3,3,4,5-hexafluoro-; Cyclobutane, 1,1,2,2,3-pentafluoro-3-(trifluoromethy) -; Cyclobutene, 3,3,4,4-tetrafluoro-1-methyl-; Cyclobutane, 1-fluoro-1-methyl-; Bicyclo(2.1.0) pentane, 2,2,3,3-tetrafluoro-; Cyclopentene, 3,3-difluoro-; 1,3-Cyclopentadiene, 5-fluoro-; Cyclobutane, 2-(difluoromethylene)- 1,1,3,3-tetrafluoro-; Spiro(2.2)pentane, 1,1,2,2,4,4-hexafluoro-; Bicyclo(1.1.1)pentane, 1-fluoro-; Cyclopentene, 4,4-difluoro-; Cyclobutane, (difluoromethylene)-; Cyclobutane, 1,1-difluoro-2-methylene-; Spiro(2.2)pentane, 1,1-difluoro-; Cyclobutane, 1,1,3,3-tetrafluoro-2-methylene-; Cyclobutane, 2-(difluoromethylene)-1,1-difluoro-, Spiro(2.2)pentane, 1,1,4,4-tetrafluoro-; Cyclopropane, 1,1-bis(trifluoromethyl)-; Spiro(2.2)pentane, 1,1,2,2- tetrafluoro-; Tricyclo(1.1.0.02.4 )butane, (trifluoromethyl)-; Spiro(2.2)pentane, 1,4-difluoro-; Spiro(2.2)pentane, 1,2-difluoro-; Spiro(2.2)pentane, fluoro-; Bicyclo(1.1.0)butane, 1-(trifluoromethyl)-; Cyclopentane, 1,2-difluoro-, cis-; Cyclopropane, (1,1, 2-trifluoroethyl)-; Cyclopropane, (1,1-difluoroethyl)-; Cyclopropane, (1,2,2-trifluoroethyl)-; Cyclopropane, (2,2-difluoroethyl)-; Cyclopropane, (2-fluoroethyl)-; Cyclopropyl, 1-fluoro-2, 2dimethyl-; Cyclopropyl, 1-fluoro-2, 3-dimethyl-, cis-; Cyclobutane, (trifluoromethyl)-; Fluoriranium, trimethyl-; Cyclopentylium, 1-fluoro-; Cyclopropane, 1,1-difluoro-2-methyl-2-(trifluoromethyl)-; Cyclopropane, 1 -fluoro-2,3-dimethyl-,(1.alpha.,2.alpha.,3.alpha.)-; Cyclopropane, 1 -fluoro-2,3-dimethyl-,(1.alpha., 2.beta.,3.beta.)-; Cyclopropane, 1-ethyl-2-fluoro-; Cyclopropane, 1-ethyl-2-fluoro-, trans-; Cyclopropane, 1-fluoro-2,3-dimethyl-,(1.alpha.,2.alpha.,3.beta.)-; Cyclobutane, 1,1,2-trifluoro-2-(trifluoromethyl)-; Cyclopropane, 1-(difluoromethyl)-1-fluoro-2-methyl-, trans-; Cyclopropane, 1-(difluoromethyl)-1-fluoro-2-methyl-,cis-; Cyclobutane, 1,1,2,2,3-pentafluoro-3-methyl-; Cyclobutane, 1,1,2,3-tetrafluoro-2-(trifluoromethyl)-; Cyclopropane, (2-fluoroethenyl)-; Cyclopropane, (1-fluoroethenyl)-; Bicyclo(2.1.0) pentane, 5,5-difluoro-; Cyclobutene, 1,4,4-trifluoro-3-methylene-; Cyclopropane, 2-etheynyl-1, 1-difluoro-, homopolymer; Cyclobutane, 3-(difluoromethylene)-1, 1-difluoro-; Cyclopropane, 1,1,2-trifluoro-2-(trifluorovinyl)-; Cyclopentene, 1-fluoro-; Cyclopropane, 2-ethyl-1, 1-difluoro-; Cyclopropene, 3,3-difluoro-1-(pentafluoroethyl)-; Cyclopropane, 1-methyl-2-(trifluoromethyl)-, cis-; Cyclopropane, 1-methyl-2-(trifluormethyl)-, trans-; Cyclopropane, 1-methylene-2-(trifluoromethyl)-; Cyclopentane, 1,1,2, 2,3,3,4,5-octafluoro-; Cyclopropane, 1-(difluoromethyl)-1-fluoro-2-methyl-, cis-; Cyclopropane, 1-(difluoromethyl)-1-fluoro-2-methyl-, trans-; Cyclopentane, 1,1,2,2,3,3,4-heptafluoro-; 1,3-Cyclopentadiene, 1,2,4,5,5-pentafluoro-, dimer; 1,3-Cyclopentadiene, 1,2,3,5,5-pentafluoro-, dimer; 1,3-Cyclopentadiene, 1,2,3,5,5-pentafluoro-; 1,3-Cyclopentadiene, 1,2,4,5,5-pentafluoro-; Cyclopentane, 1,2,3,4,5-pentafluoro-,stereoisomer; Cyclopentane, 1,1,2,3,4,5-hexafluoro-,stereoisomer; Cyclobutene, 3-fluoro-1-methyl-; Cyclopentene, 1,4,5, 5-tetrafluoro-; Cyclopentene, 3,3,4,4-tetrafluoro-; Cyclopentene, 3,3,4,4,5-pentafluoro-; Cyclopentene, 1,4,4,5,5-pentafluoro-; Cyclopentene, 1,3,3,4,4,5-hexafluoro-; Cyclopropane, (2,2,2-trifluoroethyl)-; Cyclopentane, 1,1,2,3,3,4,5-heptafluoro-; Cyclobutene, 2,3,3-trifluoro-1-(trifluoromethyl)-; Cyclopentene, 1,2, 3,3,4,5,5-heptafluoro-; Cyclopentene, 1,2,3,3,4,4,5-heptafluoro-; Cyclobutene, 3,3,4,4-tetrafluoro-1-(trifluoromethyl)-; Cyclopentene, 1,3,3,4,4,5,5-heptafluoro-; Cyclopropane, 2-fluoro-1, 1-dimethyl-; Cyclopentane, 1,1,2,2,3,4,5-heptafluoro-; Cyclobutane, 1,1,2,2-tetrafluoro-3-(trifluoromethyl)-; Cyclopentane, fluoro-; Cyclopentene, 1,2,3,3,4,5-hexafluoro-, trans-; Cyclopentane, 1,1-difluoro-; Cyclopentane, 1,1,2,3,3,4, 5-heptafluoro-, stereoisomer; Cyclopentane, 1,1,2,3,3, 4,5-heptafluoro-, stereoisomer; Cyclopentane, 1,1,2,3, 3,4,5-heptafluoro-, cis,cis-; Cyclopentene, 1,3,3,4,5,5-hexafluoro-; Cyclopentene, 1,2,3,3,4,5-hexafluoro-, cis-; Cyclopentane, 1,1,2,3,4,5-hexafluoro-, stereoisomer; Cyclopentane, 1,1,2,3,4,5-hexafluoro-, (2.alpha., 3.alpha.,4.beta.,5.alpha.)-; Cyclopentane, 1,1,2,3,4,5-hexafluoro-, stereoisomer; Cyclopentene, 1,3,4,4,5,5-hexafluoro-; Cyclopentene, 3,3,4,4,5,5-hexafluoro-; Cyclopentene, 1,2,3,4,5-pentafluoro-; Cyclopentene, 1,3,4,5,5-pentafluoro-; Cyclopentane, 1,1,2,2,3,3,4,5-octafluoro-; Cyclopentane, 1,1,2,2,3,4,4,5-octafluoro-; Cyclopentane, 1,1,2,3,4,5-hexafluoro-; Cyclopropane, 2-ethenyl-1,1-difluoro-; Cyclopropane, 1,1-difluoro-2, 3-dimethyl-, trans-; Cyclopropane, 1, 1-difluoro-2,3-dimethyl-, cis-; Cyclobutane, 1,1,2,2-tetrafluoro-3-methylene-; Cyclobutane, 1,1,2,2,3,4-hexafluoro-3-(trifluoromethyl)-; Cyclopentane, nonafluoro-; Cyclobutane, 1,1,2,2-tetrafluoro-3-methyl-; Cyclopropane, 1,2-bis (trifluoromethyl)-; Cyclobutene, 1,3,3,4,4-pentafluoro-2-methyl-; Cyclopropane, 1,1-difluoro-2,3-dimethyl-; Cyclopropane, 1-methyl-1-(trifluoromethyl)-; Cyclopropane, 1,1-difluoro-2,2-dimethyl-; 1-Butyne, 1,3,4,4,4-pentafluoro-3-(trifluoromethyl)-; 1,3-Pentadiene, 1,1,2,3,4,5,5,5-octafluoro-; Cyclobutene, 1,2,3,3,4-pentafluoro-4-(trifluoromethyl)-; 1,3-Pentadiene, 1,1,2,3,4,5,5,5-octafluoro-; Spiro(2.2 )pentane, octafluoro-; Pentadiene, octafluoro-; 1,2-Butadiene, 1,1,4.4.4-pentafluoro-3-(trifluoromethyl)-; 1,2-Pentadiene, 1,1,3, 4,4,5,5,5-octafluoro-; Cyclopropane, pentafluoro (trifluorovinyl)-; 1,3-Pentadiene, 1,1,2,3,4,5,5,5-octafluoro-; 1,4-Pentadiene, 1,1,2,3,3,4,5,5,-octafluoro-; Cyclopropene, 3,3-difluoro-1,2-bis (trifluoromethyl)-; Cyclopentene, octafluoro-; 1,3-Butadiene, 1,1,2,4,4-pentafluoro-3-(trifluoromethyl)-; Cyclobutene, 1,3,3,4,4-pentafluoro-2-(trifluoromethyl)-; 2-Pentyne, 1,1,1,4,4,5,5,5-octafluoro-; 2-Pentene, 1,1,1,2,3,4,4,5,5,5-decafluoro-; 1-Butene, 1,1,3,3,4,4, 4-heptafluoro-2-(trifluoromethyl)-; Cyclopropane, 1,1, 2,3-tetrafluoro-2,3-bis(trifluoromethyl)-, cis-; Cyclopropane, 1,1,2,3-tetrafluoro-2,3-bis (trifluoromethyl)-, trans-; 2-Pentene, 1,1,1,2,3,4,4,5,5, 5-decafluoro-; Cyclopropane, pentafluoro (Pentafluoroethyl)-; Cyclopropane, 1,1,2,3-tetrafluoro-2.3-bis(trifluoromethyl)-; Cyclopropane, 1,1,2,2-tetrafluoro-3.3-bis(trifluoromethyl)-; Cyclopentane, decafluoro-, radical ion (1-); 2-Pentene, 1,1,1,2,3,4,4, 5,5,5-decafluoro-; 2-Butene, 1,1,1,2,4,4,4-heptafluoro-3-(trifluoromethyl)-; Pentylidene, 1,2,2,3,3,4,4,5.5.5-decafluoro-; 1-Butene, 1,1,2,3,4,4,4-heptafluoro-3-(trifluoromethyl)-; Pentene, decafluoro-; Cyclobutane, heptafluoro(trifluoromethyl)-; 1-Pentene, 1,1,2,3,3,4,4, 5,5,5-decafluoro-; Cyclopentane, decafluoro-; 2-Cyclobuten-1-one, 2,3,4,4-tetrafluoro-; Furan, tetrafluoro-; Silane, tetrakis(trifluoromethyl)-; Silane, trifluoro(nonafluorobutyl)-; Pentane, 1,1,1,2,2,4,5,5,5-nonafluoro-; Pentane, 1,1,1,2,2,3,5,5,5-nonafluoro-; Pentane, 1,1,1,2,2,3,3,4,5-nonafluoro-; Pentane, 1,1,1, 2,3,3,5,5,5-nonafluoro-; Propane, 1,1,1,3,3,3-hexafluoro-2-methyl-2-(trifluoromethyl)-; Butane, 1,1, 1,2,4,4-hexafluoro-2-(trifluoromethyl)-; Pentane, 1,1,2, 2,3,3,4,4,5-nonafluoro-; Butane, 1,1,1,4,4,4-hexafluoro-2-(trifluoromethyl)-; Propane, 1,1,1,3,3,3-hexafluoro-2,2-dimethyl-; Pentane, 1,1,3,3,5,5-hexafluoro-; Butane, 1,1,1,2,3,3-hexafluoro-2-methyl-; Pentane, hexafluoro-; Pentane, 1,2,3,3,4,5-hexafluoro-; Butane, 2-(difluoromethyl)-1,1,1,2-tetrafluoro-; Butane, 1,1,1-trifluoro-2-(trifluoromethyl)-; Butane-1-13C, 4,4,4-trifluoro-3-(trifluoromethyl)-; Pentane, 1,1,1,5,5,5-hexafluoro-; Pentane, 1,1,1,2,3,3-hexafluoro-; Pentane, 2,2,3-trifluoro-; Pentane, 2,2,4-trifluoro-; Butane, 1,1,1-trifluoro-2-methyl-; Butane, 1,1,1-trifluoro-2-methyl-; Butane, 1,2,2-trifluoro-3- methyl-; Butane, 1,3,3-trifluoro-2-methyl-; Butane, 2,2,3-trifluoro-3-methyl-; Butane, 1,1,1-trifluoro-2-methyl-; Butane, 1,1,2-trifluoro-3-methyl-; Pentane, 1,1,2-trifluoro-; Propane, 1,1,1-trifluoro-2,2-dimethyl-; Pentane, 1,1,1-trifluoro-; Butane, 1,1,1-trifluoro-3-methyl-; Silane, (nonafluorobutyl)-; Silane, dimethylbis (trifluoromethyl)-; Silane, (difluoromethyl) (fluoromethyl)methyl (trifluoromethyl)-; Silane, bis (difluoromethyl)bis(fluoromethyl)-; Silane, (3,3,3-trifluoro-2-(trifluoromethyl)propyl)-; Silane, trimethyl (trifluoromethyl)-; Silane, trifluoro(1-methylpropyl); Silane, (difluoromethyl) (fluoromethyl) dimethyl-; Silane, tris(fluoromethyl)methyl-; Silane, (1,1-dimethylethyl)trifluoro-; Silane, trifluoro(2-methylpropyl)-; Silane, methyl(3.3.3-trifluoropropy)-; Silane, butyltrifluoro-.

EXAMPLE 51

In a preferred embodiment, the dispersed phase can be composed of any chemical which has a boiling point under standard pressure conditions below the body temperature of the organism to which the formulation is to be administered and which will be examined following administration by ultrasound. Example 45 discusses how one selects suitable chemicals for the dispersed phase based on the temperature range obtained by consideration of the boiling point of the selected chemical and parameters of the manufacturing process.

Fluorocarbons, because of their low toxicity, good emulsification properties, and low water solubility, leading to persistent microbubbles, are especially suitable as chemicals from which to select the dispersed phase. The following fluorocarbons are especially suitable:

1,2,2-tris (trifluoromethyl) propane.2,2-bis (trifluoromethyl) propane. 2-methyl-2 trifluoromethyl propane.tetrakis (trifluoromethyl) silane.methyl tris (trifluoromethyl) silane.bis (trifluoromethyl) dimethyl silane.trifluoromethyl trimethyl silane 1,1-bis (trifluoromethyl) -2,2,3,3-tetrafluoro cyclopropane.1,1-bis (trifluoromethyl) cyclopropane.1,1-bis (trifluoromethyl) 2,2 difluoro cyclopropane.1,1-dimethyl (–2,2,3,3)-tetrafluoro cyclopropane.2,2 difluoro 1-methyl-1-trifluoromethyl cyclopropane.1,2-bis (trifluoromethyl) -1,2,3,3 tetrafluoro cyclopropane (cis+trans).1,2-bis (trifluoromethyl) -1,2-difluoro cyclopropane (cis+trans).1,2-bis (trifluoromethyl) -3,3 difluoro cyclopropane.1,2-bis (trifluoromethyl) cyclopropane (cis+trans) 1,1,2,2,4,4,5,5-octafluoro spiro [2.2]pentane.1,1,2,2,-tetrafluoro spiro [2.2]pentane.1,1, 4,4-tetrafluoro spiro [2.2]pentane.1,1,5,5-tetrafluoro spiro [2.2]pentane.3,3,4,5 tetrafluoro furar.tris (tri fluoromethyl) phosphire.1,1,2,2,3,3,4,4,5,5, decafluoro cyclopentane 1,2,2,3,4,4,5,5-octafluoro bicyclo [1.1.1] pentane. 2,2,4,4,5,5 hexafluoro bicyclo [1.1.1] pentane.1,2,2,3,4,4-hexafluoro bicyclo [1.1.1] pentane.1,2,2,3-tetrafluoro bicyclo [1.1.1]pentane 2,2, 3,3-tetrafluoro bicyclo [1.1.1]pentane.1,2,2,3,3,4,4-pentafluoro -1-trifluoromethyl cyclobutane, 2,2,3,4,4-pentafluoro -1-trifluoromethyl bicyclo [1.1.0]butane, 2,2,4,4-tetrafluoro 1-trifluoromethyl bicyclo [1.1.0] butane.bicyclo [2.1.0]pentane.

EXAMPLE 52

The utility of high vapor pressure chemicals with boiling points above 37° C., that is, which are not low boiling liquids, as the dispersed phase component in a colloidal dispersion was tested as an ultrasound contrast agent. The following emulsions were formulated and tested according to methods described in Example 18.

| Dispersed Phase | Vapor Pressure (20° C.) | Enhancement Compared to 1-iodoperfluorooctane |
|---|---|---|
| Perfluorohexane | 150 mm Hg | 2967% |
| Perfluorooctane | 45 mm Hg | 400% |

Perfluorononane, with a vapor pressure of about 20 mm Hg at ambient temperature, would also be expected to show utility in the colloidal dispersions of this invention.

EXAMPLE 53

The objective of this study was to evaluate the potential that an intravenous administration of the emulsions of the invention, at doses effective in producing ultrasound contrast, to New Zealand White rabbits would produce the hyperinflated non-collapsible lung (HNCL) syndrome. HNCL syndrome has been produced by a number of fluorocarbon emulsions, including 20% Fluosol®, an F.D.A.-approved intravascular perfluorochemical emulsion (described in patent JP 1609986 and incorporated herein by reference), emulsions containing perfluorooctylbromide (described in patent U.S. Pat. No. 4,987,154 and incorporated herein by reference), and other fluorocarbon emulsions (described in patents or applications EP 231091, JP 63060943, U.S. Pat. No. 4,859,363, U.S. Pat. No. 5,171,755, and JP 21196730, incorporated herein by reference). The mechanism of HNCL syndrome production, its potential reversibility, and the clinical significance are not known. The syndrome is characterized by lungs which are hyperinflated at necropsy, have an increased total volume, a decreased mean density, and contain detectable quantities of the administered fluorocarbon in the tissues. Leland Clark, the discoverer of HNCL, has stated (Clark L. C., et al., Biomat., Art. Cells & Immob. Biotech., 20, 1085–1099, 1992, incorporated herein by reference) that "if HNCL occurs in other species (i.e., humans), then only fluorocarbons boiling above 150° C. can be considered safe."

Four groups of male New Zealand White rabbits (3 per group) were intravenously administered the emulsion of Example 44 at 0.2 or 1.0 mL/kg bodyweight, Fluosol (Alpha Therapeutic Corp.) at 24 mL/kg bodyweight, or saline at 24 mL/kg. The doses were selected based on a dose which produces ultrasound contrast. Body weights, food consumption, and clinical observations were made during and immediately following administration. Twenty-four hours after administration the rabbits were euthanized, the lungs excised, and the degree of inflation graded, the weights and volumes of the lungs measured, and the presence of perfluorocarbons in the tissue determined by gas chromatography, using a head space analyzer.

The lungs of rabbits receiving saline, or the emulsion of Example 44 were normal at necropsy, collapsing upon opening the thorax. The lungs of the rabbits receiving Fluosol showed moderate to severe inflation.

There were no treatment-related changes among the groups in lung weights or lung-weight-to-bodyweight ratio. The lung volume, lung-volume-to-bodyweight ratio, and lung density measurements in the rabbits administered the emulsion of Example 44 were unchanged compared to controls. The administration of Fluosol lead to a 175% increase in lung volume, a 185% increase in lung-to-body weight ratio, and a 45% decrease in lung density when compared to controls. These changes were highly significant ($p=0.001$).

Dodecafluoropentane was not detected during analysis of lung tissue from any animal in the group receiving the emulsions of Example 44. Fluosol contains four major peaks and one minor peak by gas chromatographic analysis. All five peaks were found in gas chromatograms of headspace tissue samples from animals receiving Fluosol.

Under the conditions of the study, a single administration of the emulsion of Example 44 at dosages producing excellent ultrasound contrast showed no effect on lung inflation, weight, or density, did not yield detectable levels of dodecafluoropentane in lung tissues, and is not considered to cause the hyperinflated non-collapsible lung syndrome in the rabbit.

The emulsions formed by the methods described in the prior art produced this unsafe condition at doses which were necessary to produce ultrasound contrast, while surprisingly, emulsions with fluorocarbons which boil as low as 29° C., formulated by the methods described in the instant application, did not produce HNCL.

EXAMPLE 54.

A pharmacokinetic study was performed in beagle dogs administered a single intravenous dose of the emulsion of Example 44 over 5–8 seconds at 0.05, 0.10, and 0.15 mL/kg by obtaining multiple, timed blood samples and quantifying the dodecafluoropentane content by a validated gas chromatography assay. Twenty-four dogs, twelve males and twelve females, were studied in three dosage groups.

The data was fitted to a two compartment model with a bolus input and a first order output. There was no significant difference when comparing the males and females separately or when comparing the three dosage groups.

The distribution phase varied from 0.9 to 1.3 minutes. The elimination phase varied from 30 to 48 minutes. The $t_{max}$ (time to maximum concentration in the second compartment) varied from 5.1 to 6.6 minutes. These elimination times are compared to the elimination times of fluorocarbon emulsions of the prior art which are measured in months (see Clark et al. above). Clearly an imaging agent which clears the body in a matter of hours is preferred.

EXAMPLE 55

Emulsions of dodecafluoropentane (boiling point 28°–29° C.), a mixture of dodecafluoropentane and decafluorobutane with a boiling point of 20.0° C., and perfluorocyclopentane (boiling point of 22.5° C.) were formed and their echogenicity tested. The emulsions contained Fluorad 170 C as surfactant and were formed by applying acoustic energy from a waterbath sonicator. Echogenicity was tested by adding 0.2 mL of each emulsion to 1000 mL of water at 37° C. through a 1.2 micron filter and measuring the videodensity by the methods described in Example 1. The emulsion containing dodecafluoropentane produced a grayscale intensity six seconds following administration of 58.5 units (background of 2.9), the mixture of fluorocarbons produced an increase of 3.0 to 133.3 under the same conditions, and the perfluorocyclopentane produced the greatest increase, of from 3.6 to 158.9. Thus, the lower boiling fluorocarbons produced greater echogenicity than the higher boiling fluorocarbons.

EXAMPLE 56

Useful ultrasound contrast agent formulations are formed by stabilizing dispersions of a high vapor pressure chemical with emulsions containing a dispersed phase which is composed of chemicals which themselves do not vaporize to an appreciable extent at the body temperature of an organism undergoing an ultrasound examination. For example, fluorocarbon- or hydrocarbon-containing emulsions which are composed of high boiling dispersed phases, as described in U.S. Pat. No. 4,767,410, U.S. Pat. No. 4,987,154, JP 2196730, JP 1609986, JP 63060943, and EP 245019, incorporated herein by reference can form the basis of a formulation in which the backscatter efficiency is greatly enhanced by the addition of a high vapor pressure chemical. For example, lecithin-stabilized perfluorooctylbromide emulsions have significantly increased echogenicity if perfluoroccyclopentane (boiling point=22° C.) is added to the dispersed phase prior to comminution. Other low boiling organic halides, hydrocarbons, or ethers have the same effect.

Although the invention has been described in some respects with reference to specified preferred embodiments thereof, many variations and modifications will be apparent to those skilled in the art. It is, therefore, the intention that the following claims not be given a restrictive interpretation but should be viewed to encompass such variations and modifications that may be routinely derived from the inventive subject matter disclosed.

What is claimed is:

1. A sterile colloidal dispersion for providing ultrasound contrast in a subject comprising, as the dispersed phase, dodecafluoropentane, said dodecafluoropentane being present in an amount in said dispersion such that, upon administration to said subject of said dodecafluoropentane, dodecafluoropentane gas will be present in an amount diagnostically effective for ultrasound contrast, an aqueous continuous phase, and at least one amphiphilic fluorine-containing surfactant.

2. The dispersion of claim 1 wherein said fluorine-containing surfactant comprises one or more surfactants selected from the group consisting of telomer B containing surfactants, perfluoroalkylpoly (oxyethylene) surfactants, fluoroalkylthio-ether poly (oxyethylene) surfactants, perfluoroalkylated polyhydroxylated surfactants, and mixtures thereof.

3. The dispersion of claim 1 wherein said fluorine-containing surfactant is selected from the group consisting of anionic, cationic, nonionic, and zwitterionic surfactants.

4. The dispersion of claim 1 wherein said fluorine-containing surfactant is present in a quantity sufficient to produce an interfacial tension of 26 dynes/cm.

5. The dispersion of claim 1 wherein said dodecafluoropentane is present in a concentration range of 0.00001% w/v to 166% w/v.

6. The dispersion of claim 5 wherein said dodecafluoropentane is present in a concentration range of 0.5% w/v to 5% w/v.

* * * * *